(12) United States Patent  
Florissi et al.

(10) Patent No.: US 9,031,992 B1
(45) Date of Patent: May 12, 2015

(54) ANALYZING BIG DATA

(75) Inventors: Patricia G. S. Florissi, Briarcliff Manor, NY (US); Sudhir Vijendra, Cambridge, MA (US)

(73) Assignee: EMC Corporation, Hopkinton, MA (US)

(*) Notice: Subject to any disclaimer, the term of this patent is extended or adjusted under 35 U.S.C. 154(b) by 169 days.

(21) Appl. No.: 13/249,335

(22) Filed: Sep. 30, 2011

(51) Int. Cl.
*G06F 7/00* (2006.01)
*G06F 17/30* (2006.01)

(52) U.S. Cl.
CPC ..................................... *G06F 17/30* (2013.01)

(58) Field of Classification Search
None
See application file for complete search history.

(56) References Cited

U.S. PATENT DOCUMENTS

| | | | | |
|---|---|---|---|---|
| 2005/0055368 | A1* | 3/2005 | Bruening et al. | 707/102 |
| 2008/0040347 | A1* | 2/2008 | Potok et al. | 707/6 |
| 2010/0332531 | A1* | 12/2010 | Galande | 707/770 |
| 2011/0191343 | A1* | 8/2011 | Heaton et al. | 707/737 |

* cited by examiner

*Primary Examiner* — Rehana Perveen
*Assistant Examiner* — Raheem Hoffler
(74) *Attorney, Agent, or Firm* — Krishnendu Gupta; Joseph D'Angelo

(57) ABSTRACT

A method, apparatus, and computer implemented method for analyzing a Big Data dataset, the method comprising performing analysis on a big data dataset by applying a set of analytical tool to a Big Data Model; wherein the Big Data Model decouples the Big Data dataset into properties and metadata; wherein each of the properties represent part of the Big Data dataset to enable processing and analysis; wherein the metadata enables calculation of summary information for the Big Data dataset.

20 Claims, 26 Drawing Sheets

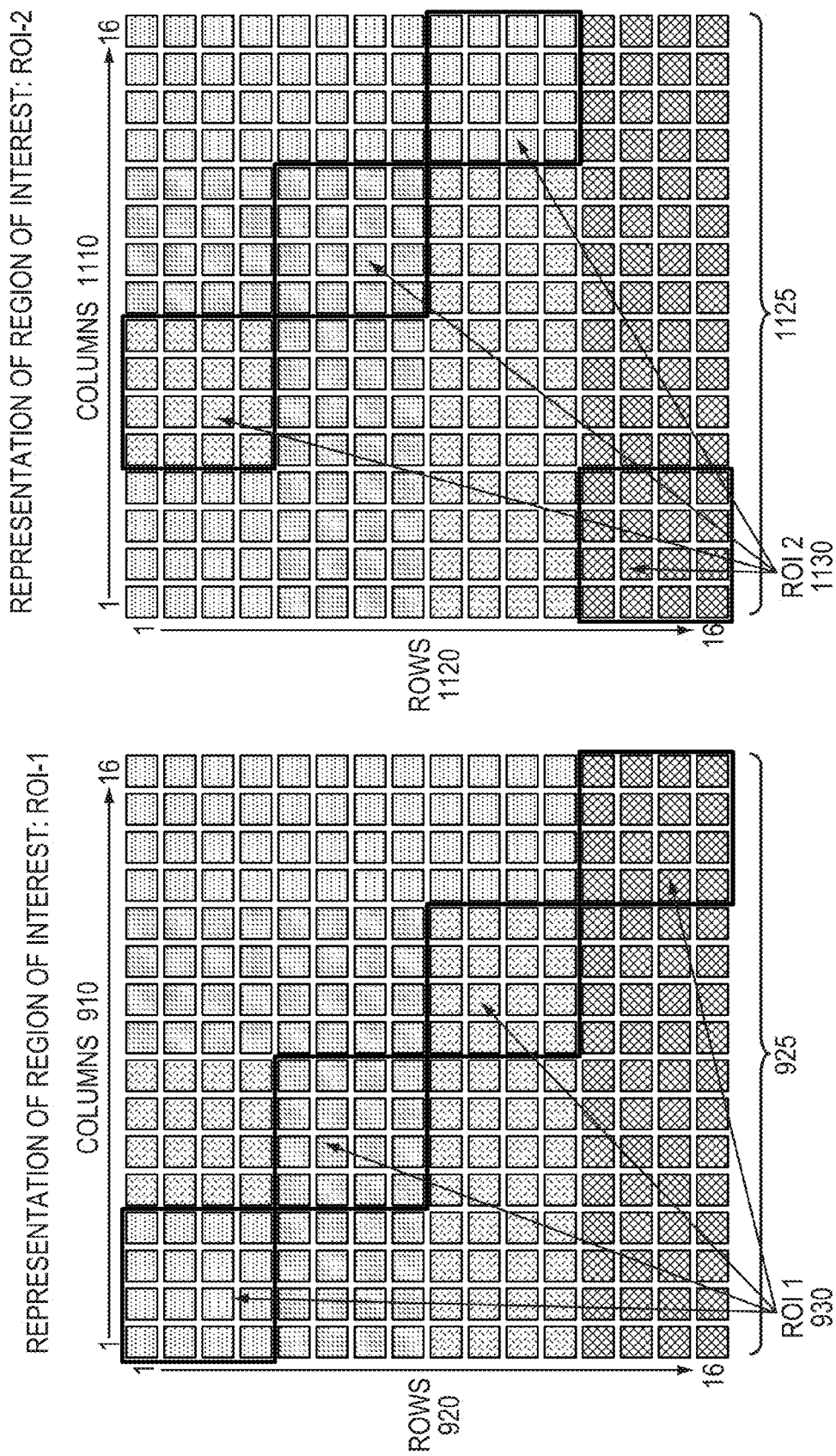
FIG. 8-I

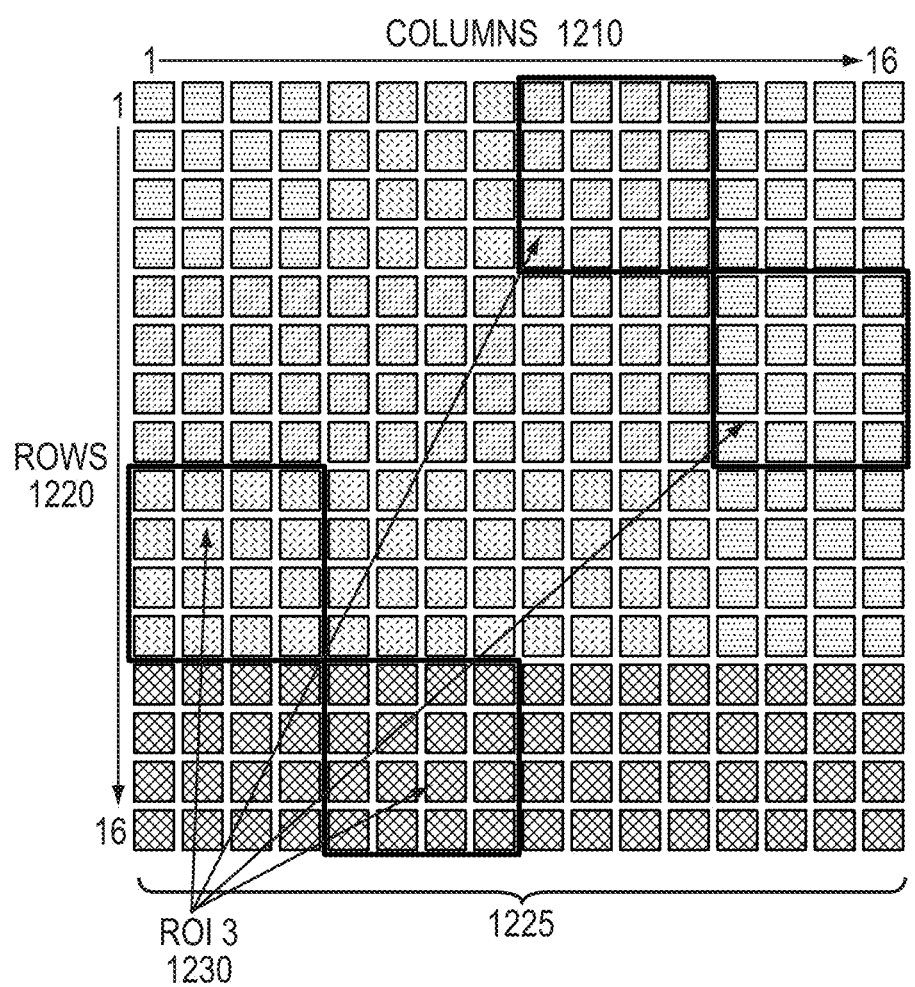
FIG. 8-II

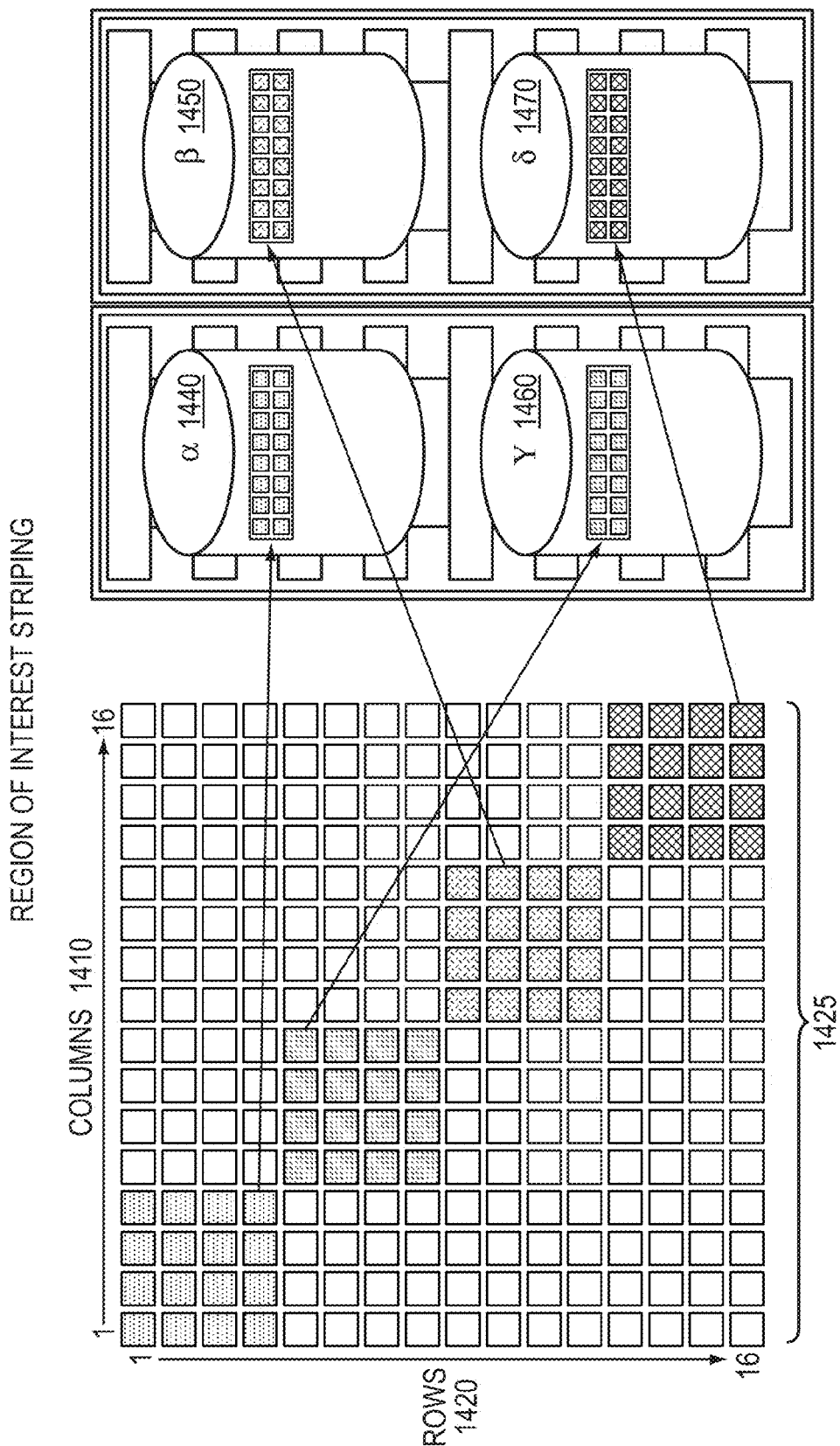
FIG. 9-I

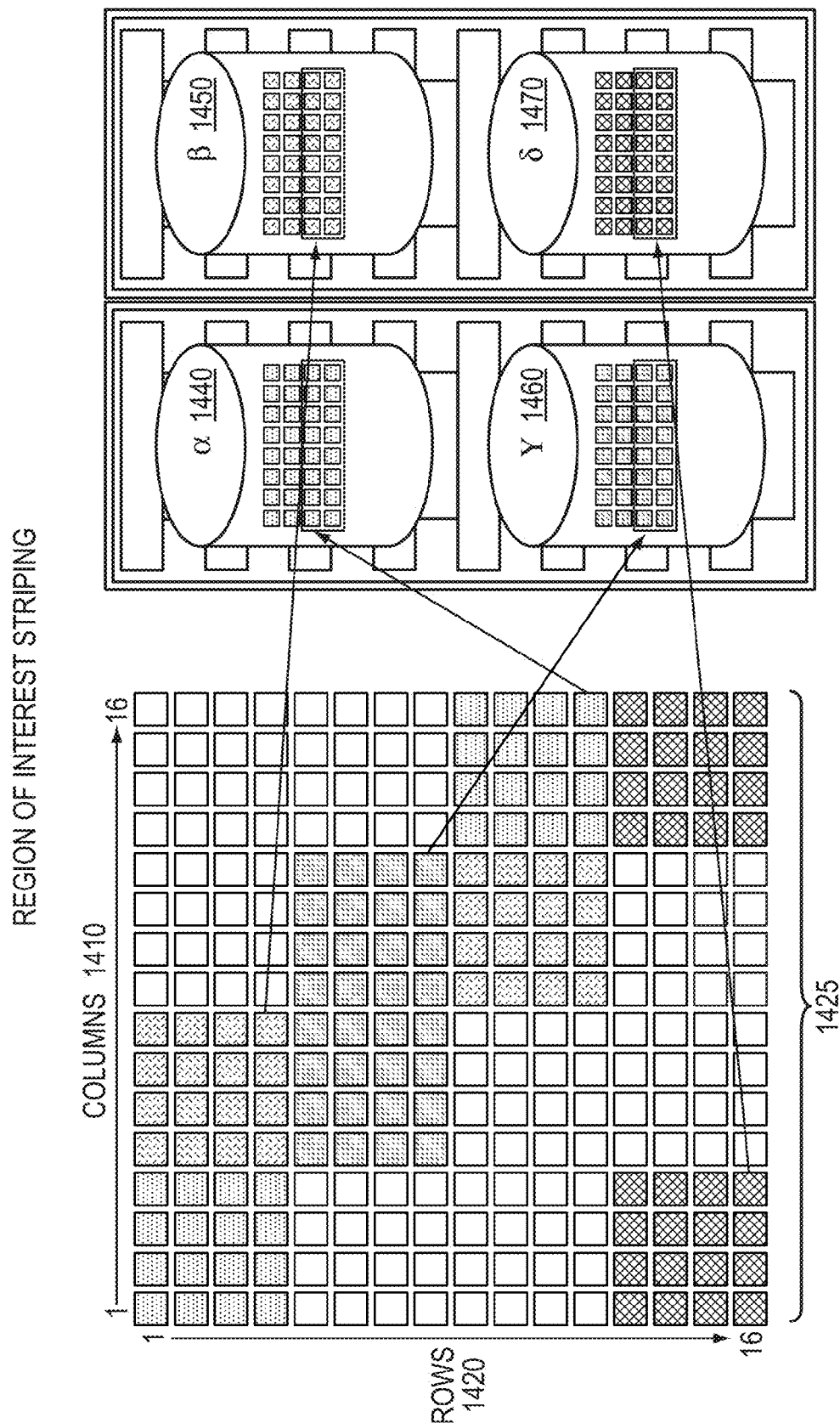
FIG. 9-II

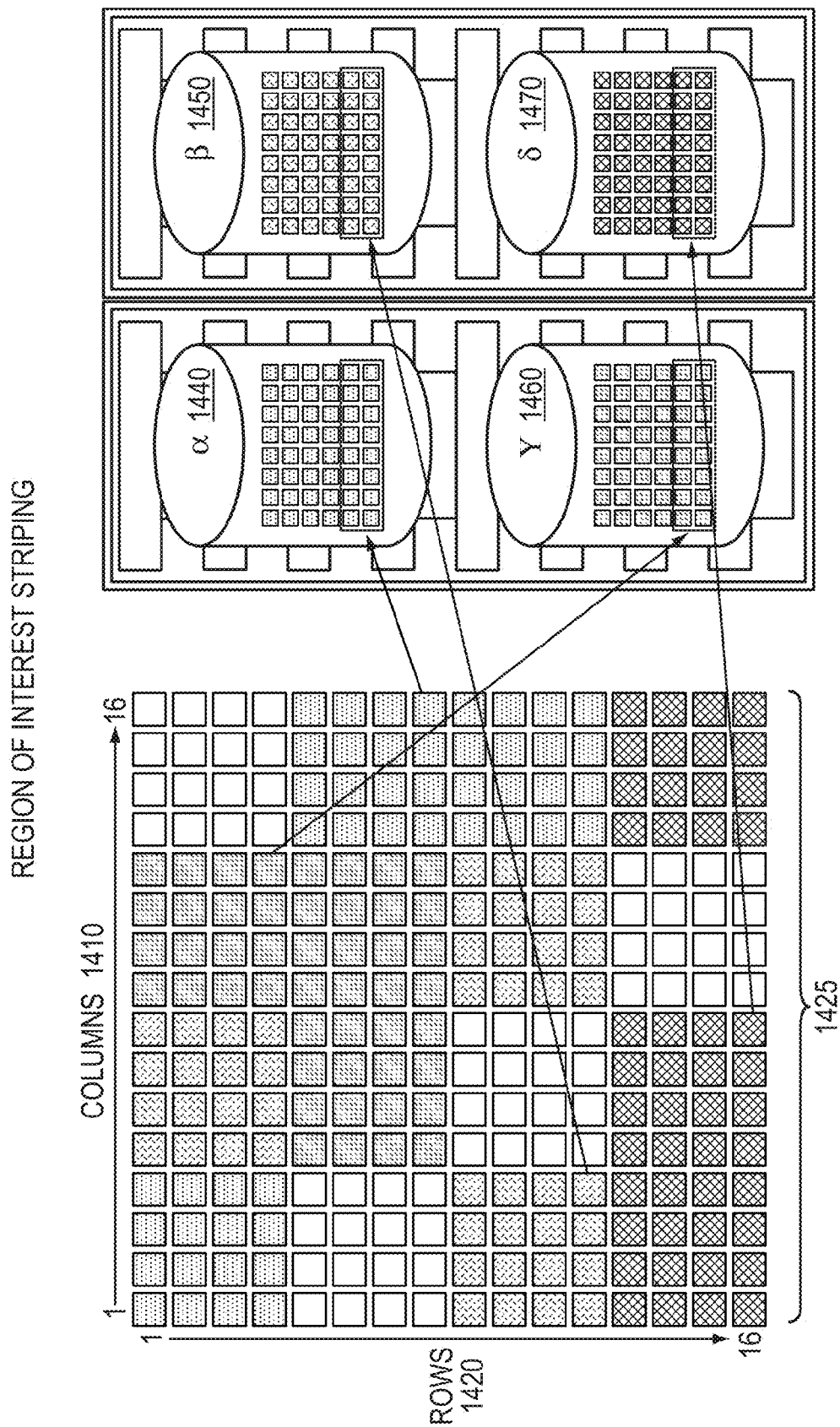
FIG. 9-III

MetaInformation:: MetaInfo-100GB-Images 1105

Attributes 1110 :
1. Sources
2. CreationTime
3. FileFormat
4. Blocks
5. ObjectStore
6. DataBase-Type
7. Linked-Metadata-List
8. GrowthRate
9. LastUsed
10. Analysis-Type-List
11. Analysis-Policy-List
12. Compute-Resource-Used

FIG. 11

ANALYZING BIG DATA

A portion of the disclosure of this patent document may contain command formats and other computer language listings, all of which are subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

RELATED APPLICATIONS

This application is related to co-pending U.S. patent application Ser. No. 13/249,330 entitled "MODELING BIG DATA," filed on even date herewith. The contents of which are hereby incorporated by reference.

TECHNICAL FIELD

This invention relates to Big Data.

BACKGROUND

The amount of data in our world has been exploding. Companies capture trillions of bytes of information about their customers, suppliers, and operations, and millions of networked sensors are being embedded in the physical world in devices such as mobile phones and automobiles, sensing, creating, and communicating data. Multimedia and individuals with smartphones and on social network sites will continue to fuel exponential growth. Yet, the impact this growing amount of data will have is unclear.

SUMMARY

A method, apparatus, and computer implemented method for analyzing a Big Data dataset, the method comprising performing analysis on a big data dataset by applying a set of analytical tool to a Big Data Model; wherein the Big Data Model decouples the Big Data dataset into properties and metadata; wherein each of the properties represent part of the Big Data dataset to enable processing and analysis; wherein the metadata enables calculation of summary information for the Big Data dataset.

DESCRIPTION OF DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every figure. The drawings are not necessarily to scale, emphasis instead being placed upon illustrating embodiments, principles, and concepts. Thus, features and advantages of the present disclosure will become more apparent from the following detailed description of exemplary embodiments thereof taken in conjunction with the accompanying drawings in which:

FIG. 8*i* is a simplified illustration of a region striping of areas of interest, in accordance with an embodiment of the present disclosure;

FIG. 8*ii* is a simplified illustration of a region striping of areas of interest, in accordance with an embodiment of the present disclosure;

FIG. 9*i* is a simplified illustration of a region striping of areas of interest across storage mediums, in accordance with an embodiment of the present disclosure;

FIG. 9*ii* is an alternative simplified illustration of a region striping of areas of interest across storage mediums, in accordance with an embodiment of the present disclosure;

FIG. 9*ii* is a further alternative simplified illustration of a region striping of areas of interest across storage mediums, in accordance with an embodiment of the present disclosure;

FIG. 11 is a simplified illustration of a model representation of a Big Data MetaInformation, in accordance with an embodiment of the present disclosure;

DETAILED DESCRIPTION

Figure 1:
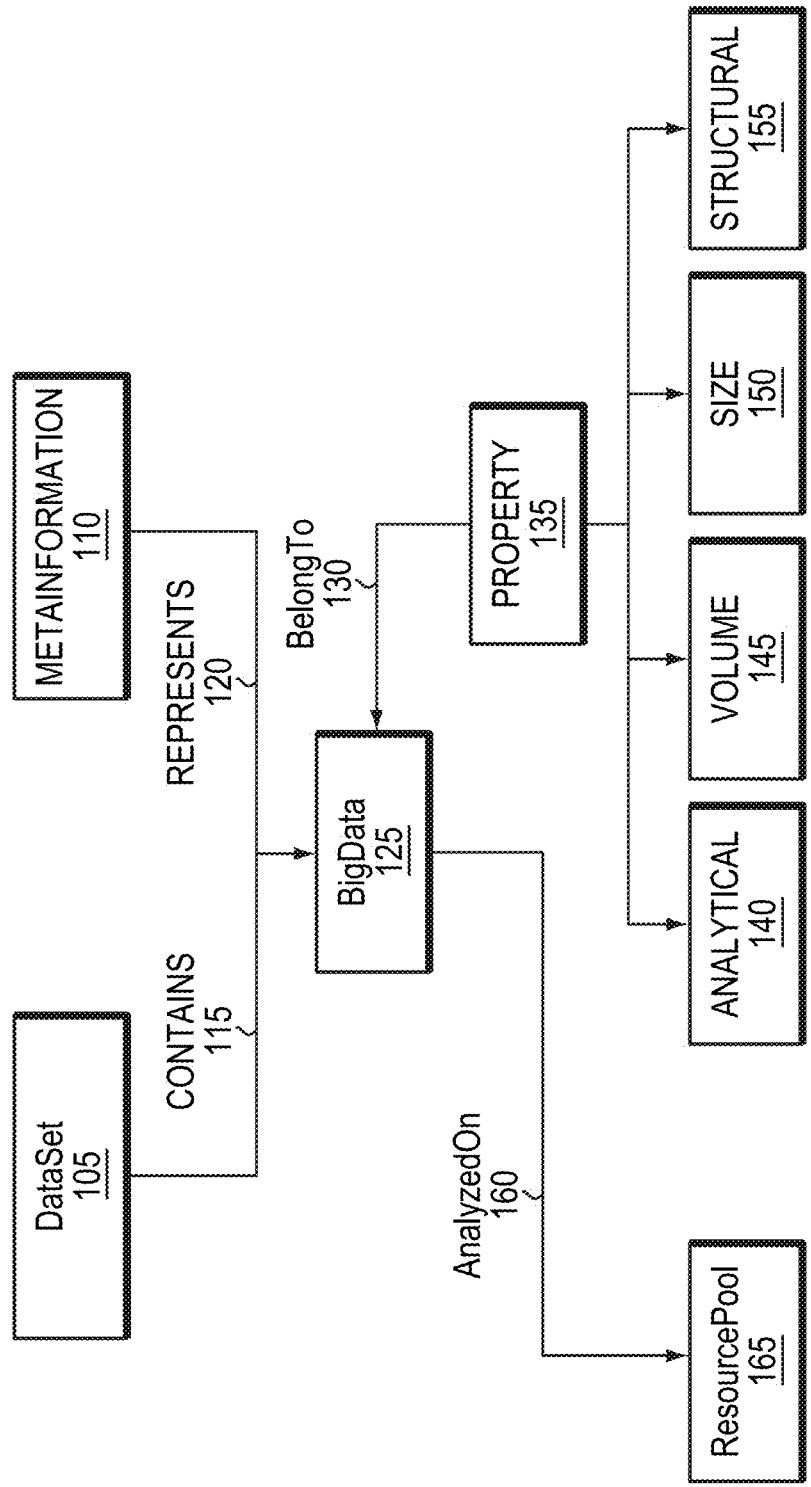
FIG. 1 is a simplified illustration of a model representation of Big Data, in accordance with an embodiment of the present disclosure.

Generally, the amount of data capture has grown in every area of global economy. Normally, companies are churning out increasing amounts of transactional data, capturing trillions of bytes of information about their customers, suppliers, and operations. Conventionally, millions of networked sensors embedded in the physical world in devices such as mobile phones, smart energy meters, automobiles, and industrial machines create data that is recorded and stored. Usually, as companies and organizations generate a tremendous amount of digital data that are created as a by-product of their activities. Often, enterprises may be collecting data with greater granularity and frequency, capturing every customer transaction, attaching more personal information, and also collecting more information about consumer behavior in many different environments. Usually, this activity increases the need for more storage and analytical capacity.

Typically, social media sites, smartphones, and other consumer devices including PCs and laptops have allowed billions of individuals around the world to contribute to the amount of data available. Normally, consumers communicate, browse, buy, share, and search creating large amounts of consumer data. However, conventional techniques are not able to monitor or analyze this "Big Data." Generally, conventional modeling techniques do not accommodate for or do not model the properties that define Big Data. For example, conventional techniques may not be able to perform analysis on Big Data because of the sheer number and size of transaction that would be necessary to perform the analysis. As well, conventional techniques may consider elements as attributes of the data when, to properly represent the Big Data these "attributes" may need to be considered as properties of the Big Data.

In some embodiments, "Big Data" may refer to a dataset that has a size, volume, analytical requirements, or structure demands larger than typical software tools can capture, store, manage, and analyze. In certain embodiments, "Big Data" may refer to a dataset that has a combination of attributes, such as size, volume, structure, or analytical requirements, with which typical software tools may not be able to work. In most embodiments, big data is not defined in terms of being larger than a certain number of terabytes rather, as technology advances over time, the size of datasets that qualify as big data may also increase.

In further embodiments, the definition of "Big Data" may vary by sector or industry, depending on what kinds of software tools are commonly available and what sizes of datasets are common in a particular industry. Big Data may refer to data from Digital Pathology, data from seismological surveys, data from the financial industry, and other types of data sets that are generally too large, for example in size or number of transactions, to be modeled an analyzed with conventional techniques.

In some embodiments of the current disclosure, a big data model is presented to enable Big Data to be modeled and analyzed. In other embodiments of the current disclosure, a set of computer implemented objects are enabled which represent the Big Data elements and relationships within a model on one or more computers. In certain embodiments, the model may include representations of the hierarchy and classification of metadata of the Big Data sets. In other embodiments, the model may map the metadata or data set to the resources needed to analyze data Big Data domain. In certain embodiments, the model may acknowledge and accommodate for the complexity of the Big data set. In most embodiments, the current techniques enable representation of the size, volume, structure, and analytical requirements to enable the Big Data to be modeled an analyzed.

In an embodiment, the current techniques may acknowledge that the Big Data set may need to be modeled and analyzed semantically. In another embodiment, the current techniques may acknowledge that the data set is too large for normal modeling. In a further embodiment, the current techniques may model and analyze the Big Data in an unstructured way. In further embodiments, the current techniques may combine the different requirements of the Big Data set, such as a large transactional dataset which may need to be analyzed in an un-semantic manner to enable modeling and analysis of this Big Data. In certain embodiments, the current techniques may decouple elements as attributes of the data and represent these "attributes" as properties of the Big Data. In an embodiment, the current techniques may enable analyzing structural, semantical, and syntactical properties of the data. In further embodiments, the current techniques may analyze the semantical properties in terms of the syntactical properties of the data. In some embodiments, properties and meta information associated with Big Data may be used during runtime to decide where to store the information as well as the type of resource pool to be allocated with the Big Data depending on the type of analysis to be done with the data.

Referring to FIG. 1, this figure illustrates an exemplary abstract model for Big Data in accordance with the current disclosure. The classes, objects, and representations shown in the model may be an extension of known distributed system models, such as the EMC/Smarts Common Information Model (ICIM), or similarly defined or pre-existing CIM-based model and adapted for the environmental distributed system, as will be discussed. EMC and SMARTS are trademarks of EMC Corporation, Inc., having a principle place of business in Hopkinton, Ma, USA. This exemplary model is an extension of the DMTF/SMI model. Model based system representation is discussed in commonly-owned U.S. patent application Ser. No. 11/263,689, filed Nov. 1, 2005, and Ser. No. 11/034,192, filed Jan. 12, 2005 and U.S. Pat. Nos. 5,528, 516; 5,661,668; 6,249,755 and 6,868,367, and 7,003,433, the contents of all of which are hereby incorporated by reference. An example of a Big Data Set may be found in commonly-owned U.S. patent application Ser. No. 12/977,680, filed Dec. 23, 2010, entitled "INFORMATION AWARE DIFFERENTIAL STRIPING" the contents of which are hereby incorporated by reference.

Generally, referred-to US Patents and patent applications disclose modeling of distributed systems by defining a plurality of network configuration non-specific representations of types of components (elements or devices) managed in a network and a plurality of network configuration non-specific representations of relations among the types of managed components and problems and symptoms associated with the components and the relationships. The configuration non-specific representations of components and relationships may be correlated with a specific Big Data set for which the associated managed component problems may propagate through the analyzed system and the symptoms associated with the data set may be detected an analyzed. An analysis of the symptoms detected may be performed to determine the root cause—i.e., the source of the problem—of the observed symptoms. Other analysis, such as impact, fault detection, fault monitoring, performance, congestion, connectivity, interface failure, in addition to root-cause analysis, may similarly be performed based on the model principles described herein.

Modeling

Refer again to the example embodiment of FIG. 1. FIG. 1 illustrates an example embodiment of a data hierarchy for a model that may be used to model Big Data. In this embodiment, a data set may have one or more properties that are bigger in size or volume or analytical properties that may normally be modeled. In FIG. 1, DataSet 105 Contains 115 Big Data 125 and MetaInformation 110 Represents 120 Big Data 125. Meta Information 110 may be classes or objects that hold key attributes of Big Data 125 which may be used for a quick analysis.

Big Data 125 may also have Properties 135 which Belong To 130 Big Data 135. Properties 135 may contain properties that are Analytical 140, Volume 145, Size 150, and Structural 155. In some embodiments, there may be an analytical property, which may be a class or object that contain Transactional Properties or Quantitative/Numerical Properties or Iterative or HPC properties to the purpose of analytics and reporting. In certain embodiments, there may be a volume property class or object which may contain the information of List or Hierarchical or Sequential or Mash or Blogs. Big Data 125 may be Analyzed On 160 Resource Pool 165. Resource Pool 165 may represent the available computing, storage and network resources, physical and virtual, for the purpose of analysis, storage, and transfer of the analyzed information.

Figure 2:
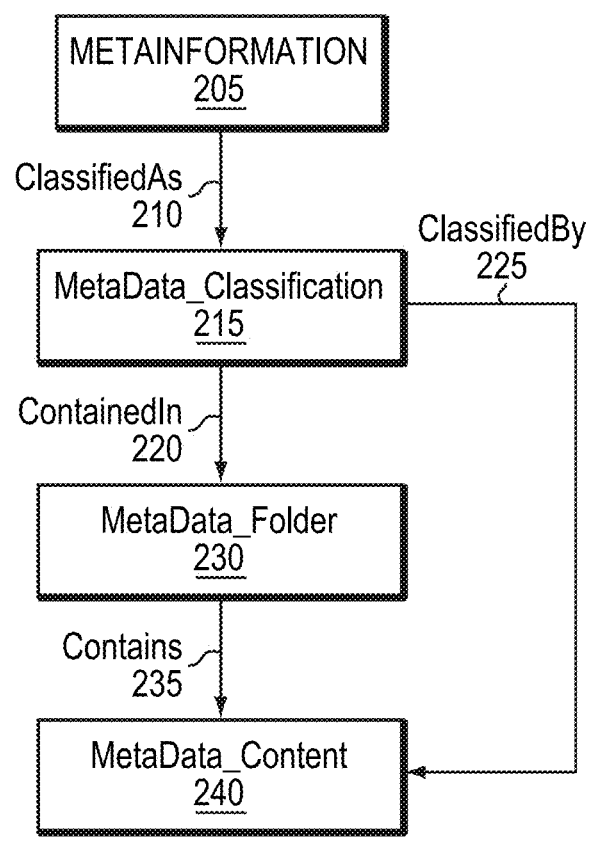
FIG. 2 is a simplified illustration of a model representation of a MetaData classification for Big Data, in accordance with an embodiment of the present disclosure.

Refer now to the example embodiment of FIG. 2. FIG. 2 illustrates some objects and representations that may be useful in modeling big data. Meta Information 205 may be Classified As 210 Meta Data Classification 215 which may be Contained In 220 Metadata Folder 230, which Contains 235 metadata content 240. Metadata classification 215 may be Classified by 225 Metadata Content 240.

In some embodiments, Meta Information may have a set of key attributes. In some embodiments, the set may include some or all of the attributes of sources, creation time, file format, blocks, object store, DataBase-Type, Linked-Metadata-List, growth rate, last used, analysis-Type-List, analysis-Policy-List, compute-Resource-Used.

Figure 3:
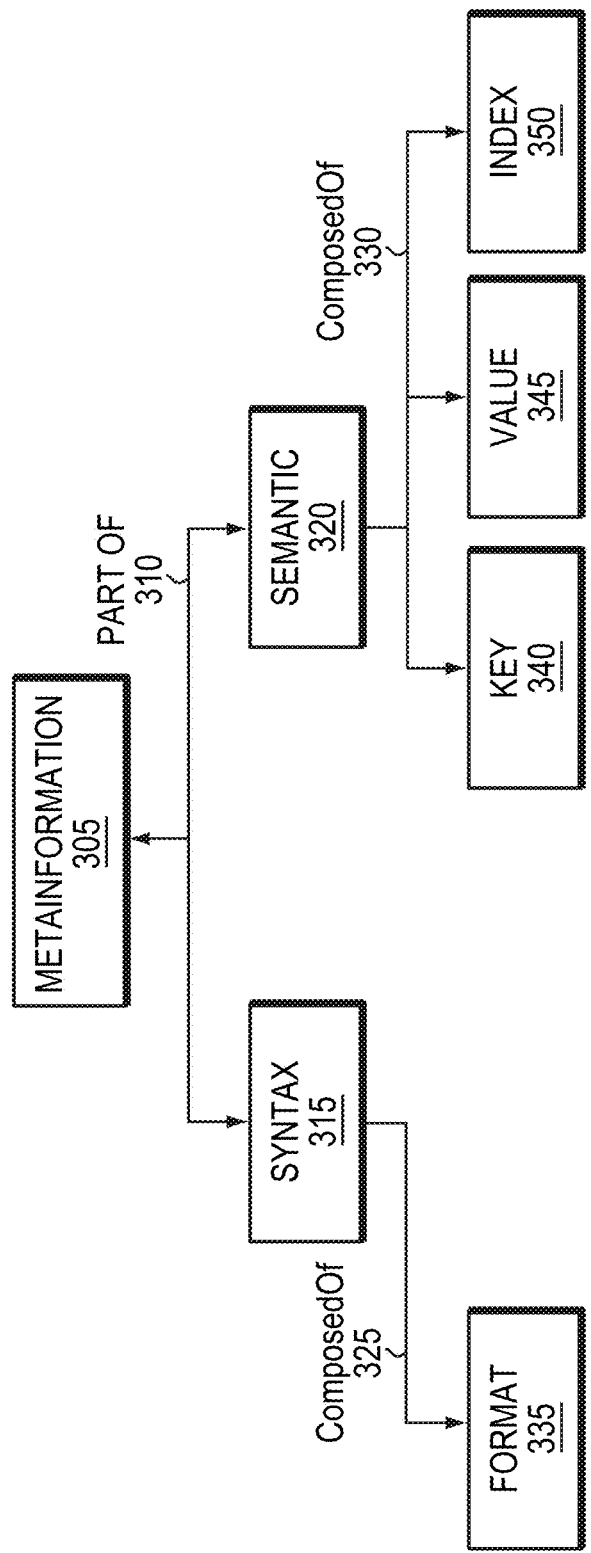
FIG. 3 is a further simplified illustration of a model representation of metadata information for Big Data, in accordance with an embodiment of the present disclosure.

Refer now to the example embodiment of FIG. 3. FIG. 3 illustrates some objects and representations that may be useful in modeling big data. In FIG. 3, MetaInformation 305 may be Part Of 310 Syntax 315 and Semantic 320 and may be a class or object that holds the key information about the big data. Syntax 315 may be a class or object that represents the syntactic meta information of the big data. In FIG. 3, Syntax 315 may be Composed Of 325 Format 335. In the example embodiment of FIG. 3, Format 335 may be a class or object which represents the format in which data is formatted. In the embodiment of FIG. 3, Format 335 may also specify an algorithm or general pattern. Semantics 320 may be a class that represents the semantics of the big data. Semantic 320 may be Composed Of 330 Key/Value Pair 340, 345, which may be a class or object which helps to decipher the meaning of the big data based on key/value of certain information. Semantic 320 may also be Composed Of 330 Index 350. Index 350 may be a class or object that points to a specific meaning for the purposes of semantic look ups.

Figure 4:
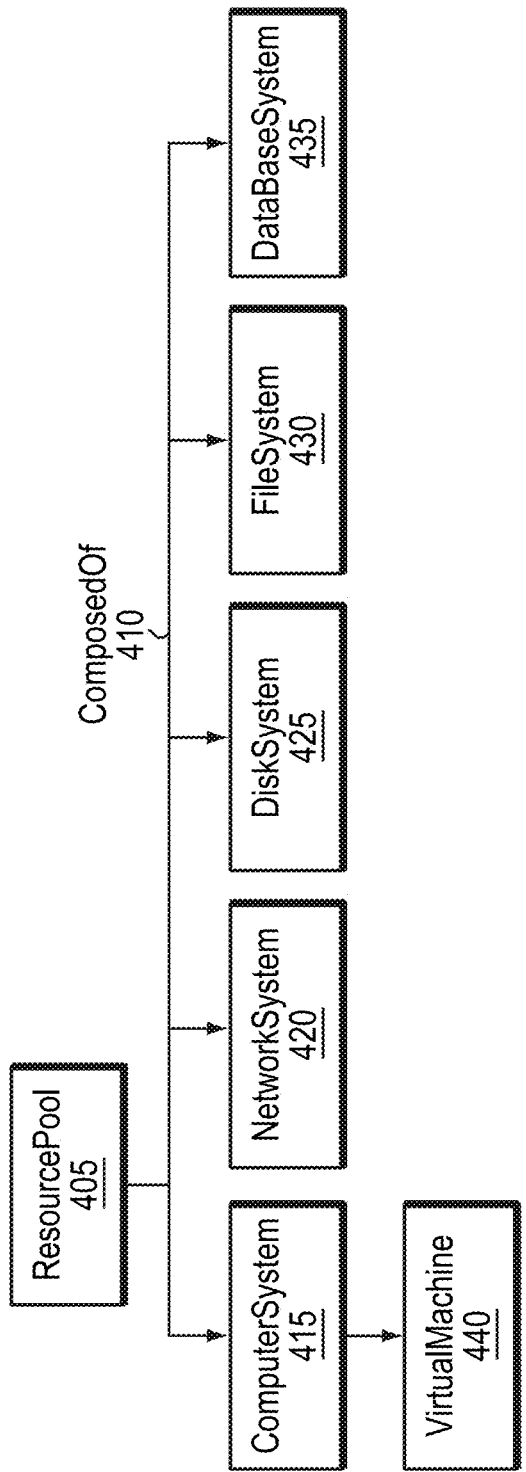
FIG. 4 is a simplified illustration of a model representation of a Resource Pool for Big Data, in accordance with an embodiment of the present disclosure.

Refer now to the example embodiment of FIG. 4. FIG. 4 illustrates some objects and representations that may be useful in modeling big data. Resource Pool 405 may be Composed Of 410 Computer System 415, which may in turn be Virtual Machine 440, Network System 420, Disk System 425, File System 430, and Database System 435. Generally the representations that compose the resource pool may be the resources available for the system to analyze the big data.

Figure 5:
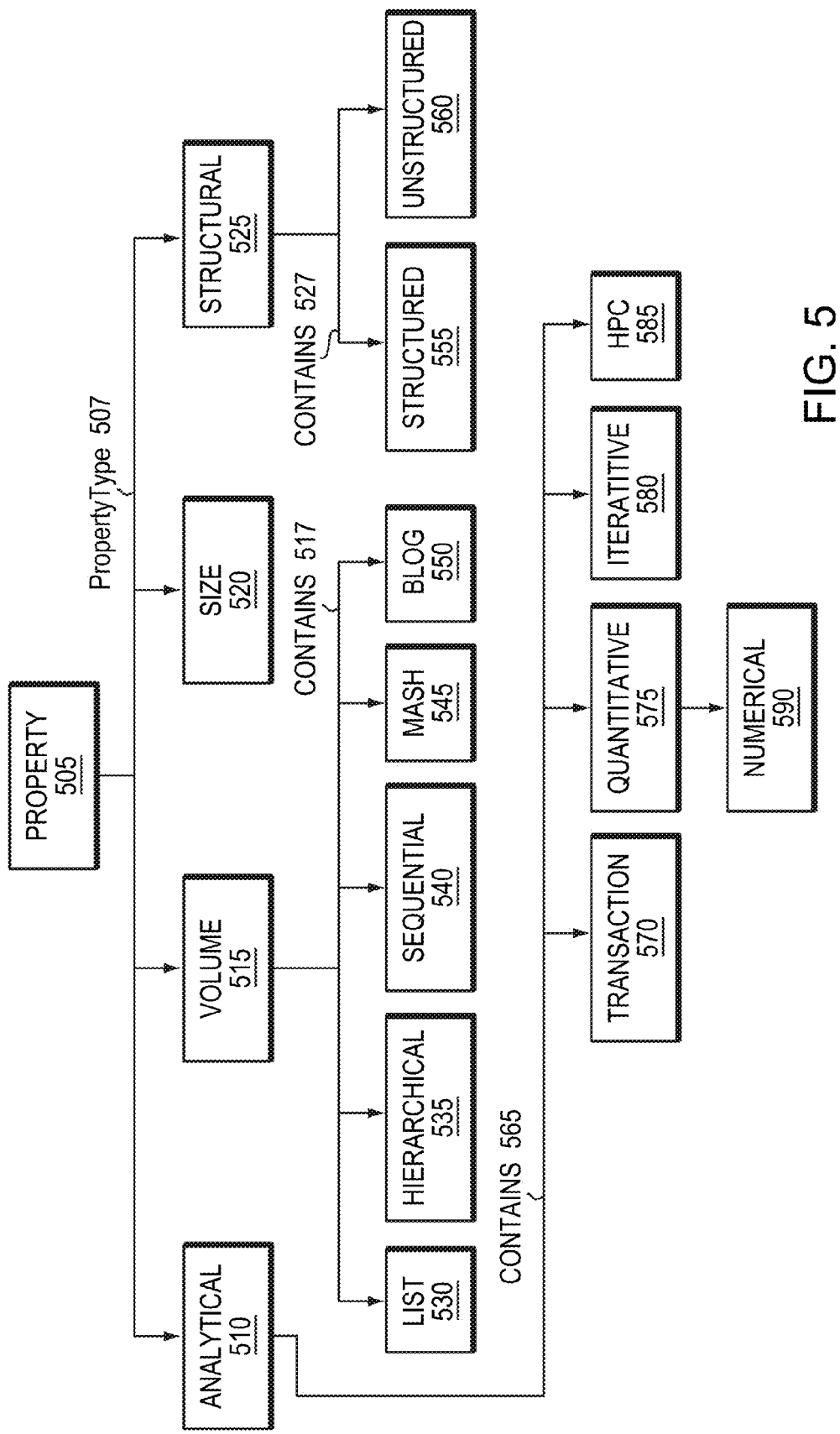
FIG. 5 is a simplified illustration of a model representation of a Property Model for Big Data, in accordance with an embodiment of the present disclosure.

Refer now to the example embodiment of FIG. 5. FIG. 5 illustrates some objects and representations that may be useful in modeling big data. Big Data Property 505 may have Property Type 507 Analytical 510, Volume 515, Size 520, and Structural 525. Size 520 may indicate that the data is generally beyond typical database capacity. Size 520 may be an object or class that may generally be defined only based on the size of the data.

Volume 515 may Contains 517 List 530, Hierarchical 535, Sequential 540, Mash 545 and Blog 550. Volume 515 may represent an object or class that could be classified by the property of volume. List 530 may represent list data. Hierarchical 535 may represent hierarchical nature of data, which may be heavily organized data. Sequential 540 may be an object or class representing that the list of data is ordered sequentially. Mash 545 may be a class or object that represents the data that comes from one or many sources. Blog 550 may represent data that comes from blogs with many activities such as posting and responses. In certain embodiments, the same Big Data may have multiple Volume properties objects referring to it, as a Big Data may contain multiple of these properties simultaneously. In some embodiments, a Big Data may be Contain characteristics of a Blog, and Sequential properties.

Structural 525 may refer to data that may be better treated and analyzed based on storage type, either stored in fixed fields of databases or in unstructured formats. Structural 525 may Contains 527 Structured 555 and Unstructured 560 data. In most embodiments, two classes or objects may be used to represent data based on the data if it can be fixed in the data base field. If the data can be fixed in a DB field then the data is can be represented using the structured class, otherwise the data may be unstructured. Structured data 555 may be data may be better treated and analyzed based on storage type, fixed fields of databases. Unstructured 560 may be data that may be better treated and analyzed based on storage type, unstructured formats. In certain embodiments, Big Data may contain parts of the data that may be structured and other parts that may be unstructured. In a particular embodiment, a Blog file may contain a Structured part representing the date, time, and IP address of sender, and an unstructured part containing the actual content of the data. Analytical 510 may Contains 565 Transaction 570, Quantitative 575, Iterative 580, and High Performance Computing (HPC) 585. Quantitative 575 may have Numerical 590. Transactional Properties 570 may represent the transactions and may include retail and financial transactions that could be used for further analytics. Quantitative 575 and Numerical Properties 590 may represent scientific quantitative properties or other numerical data such as data used to calculate oil fields extraction analysis. Iterative 580 may represents data that is repetitive or iterative in nature such as data repetitions due to compressions algorithm. HPC 585 may represents the need of high performance computing, usually a scientific application.

In some embodiments to build a topology for a Big Data model, class instances may be generated. In certain embodiments, status may be assigned to the model and big data and attributes and types may be created. In certain embodiments, relationships may be built. In further embodiments, relationships may be inferred. In most embodiments, redundant classes may be optimized. In most embodiments, redundant relationships may be optimized.

Take for example, a digital pathology sample that may have a size of 5 gb. However, only specific regions of the image may be of interest to application clients (i.e. a medical pathologist). Typically, only information associated with the area of interest may be needed. As well as a particular region is examined, a user may zoom in into the area of interest and more meta-information about the area of interest for the region may be required. Similarly, users examining pictures for friends may only be interested in images that contain the faces of their friends. Thus, it may be advantageous to the user to load the portions of the images that have the faces first, then the load the rest of the images. As well, a user examining a map may be interested in a particular portion of the map to determine whether or not the user wants to zoom in on this area. Thus, it may be advantageous to load the area of interest on the map first, before loading the other portion of the map.

Typically, some types of images have different contextual layers and it may be advantageous to be able to quickly shift between these contextual layers. Generally, the portions of the contextual layers that may be important are the contextual layers associated with a region of interest. For example, a user may want to shift between different contextual views of a pathology image, such as views of the sample taken under different frequencies of light. However, applying the current techniques to the image would enable metadata properties that indicate only certain areas of interest should be analyzed, i.e. the marked regions of interest. The meta data could further indicate the portions of the image which represent the areas of interest under different lights. An image from digital pathology may be sparse with one or more Regions of Interest (ROI). That is, the image may have many areas which do not contain information of interest and a few regions that contain the part of the image a pathologist may wish to examine.

Figure 6:
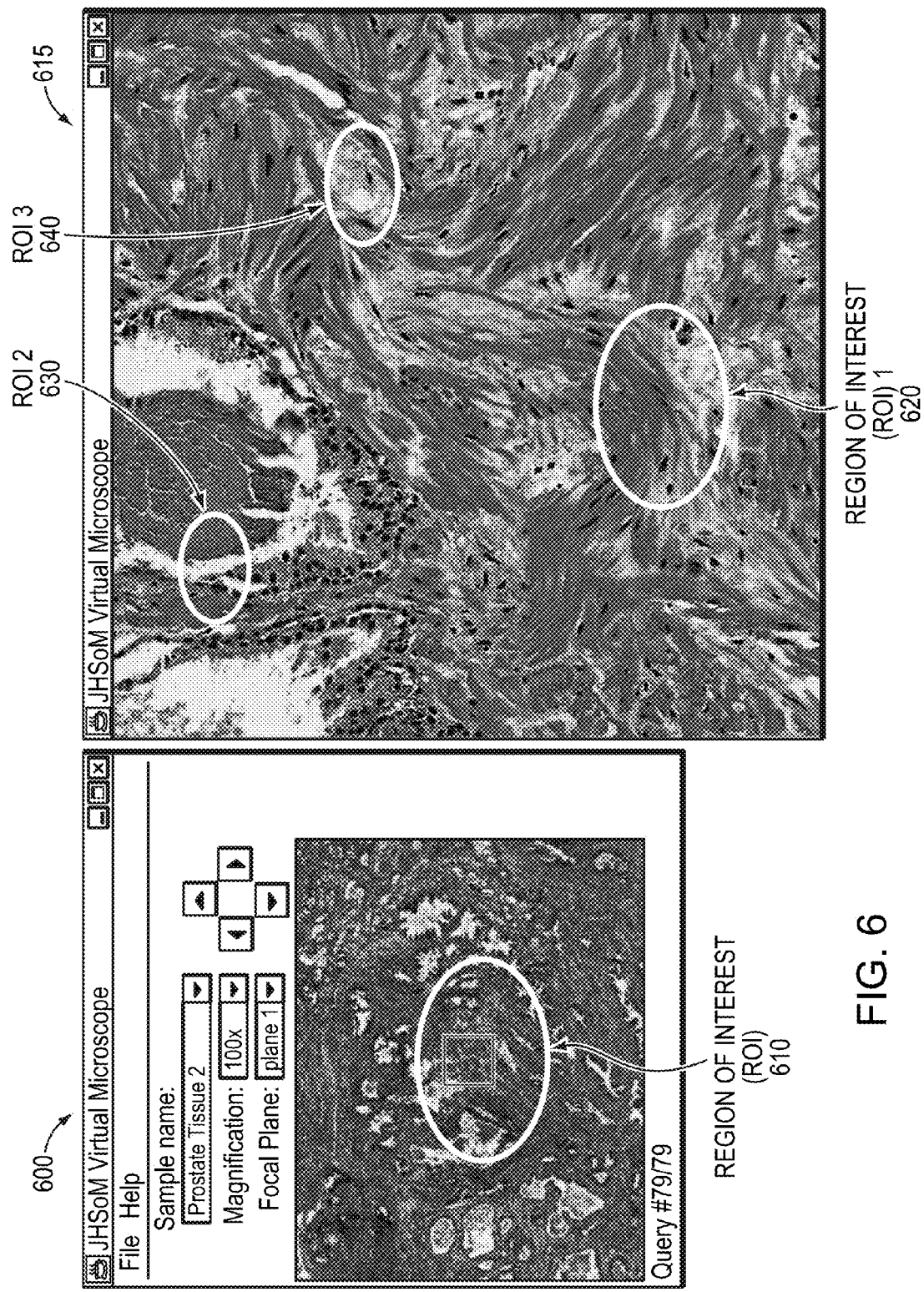
FIG. 6 is a simplified example of regions of interest for a digital pathology slide, in accordance with an embodiment of the present disclosure.

For example, refer to the example embodiment of FIG. 6. FIG. 6 illustrates a particular ROI for a digital pathology image and several other ROI in a larger image. Quick access to the ROI may not fit well into any of the previous example methods of stripping, which may not be based on metadata. This may be because without specific information about how to store or retrieve the information about the ROI, the ROI may be loaded as any other portion of the image.

Figure 7:
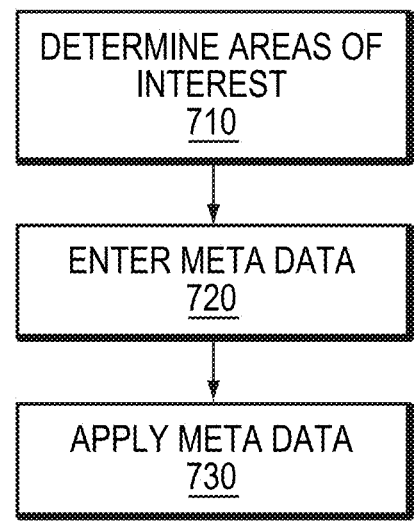
FIG. 7 is a simplified method for use in modeling Big Data, in accordance with an embodiment of the present disclosure.

However, it may be advantageous to first load the areas of interest and then load the other sparse areas of the images. Thus, an embodiment of the current disclosure enables stripping of the image based on contextual information to enable faster loading of the ROI. For example, consider the example embodiments of FIGS. 7 and 8 *a-c*. The highlighted blocks of FIG. 8 *a-c* may be identified to represent region of interests ROI 1-3 (step 710). Each of the blocks corresponds to a different piece of the ROIs. For this image, metadata may be entered which describes the ROIs (step 720). Now refer as well to FIG. 9. The metadata may be applied to the image so that each of the blocks is stored in different storage medium, such as 940, 950, 960, and 970 to impact image retrieval (step 730).

When the image is loaded, the contextual information may be leveraged to quickly load the ROI before loading the rest of the image. Thus, the ROIs may be loaded and displayed first followed by other ROIs and then the rest of the image. The contextual information, such as which portion of the image corresponds to the ROI may be stored in metadata associated with the image.

However, it may be advantageous to first load the areas of interest and then load the other sparse areas of the images. Thus, an embodiment of the current disclosure enables stripping of the image based on contextual information to enable faster loading of the ROI. The layout of image 925 across storage mediums 940, 950, 960, and 970 based on the ROI may enable quick access, loading, and switching between ROIs.

Refer now to the example embodiments of FIG. 9*a-c*. FIGS. 9*a-c* illustrate a particular mapping of the regions of interest across the storage medium to enable quick access to ROI 1-3. In these examples, the metadata or contextual information impacted the storing of the data on the storage mediums according to the ROIs. This enabled the information to be stored by striping the ROI across the storage mediums so that when the image is accessed, the ROIs may be accessed first and more quickly based on the striping.

Figure 10:
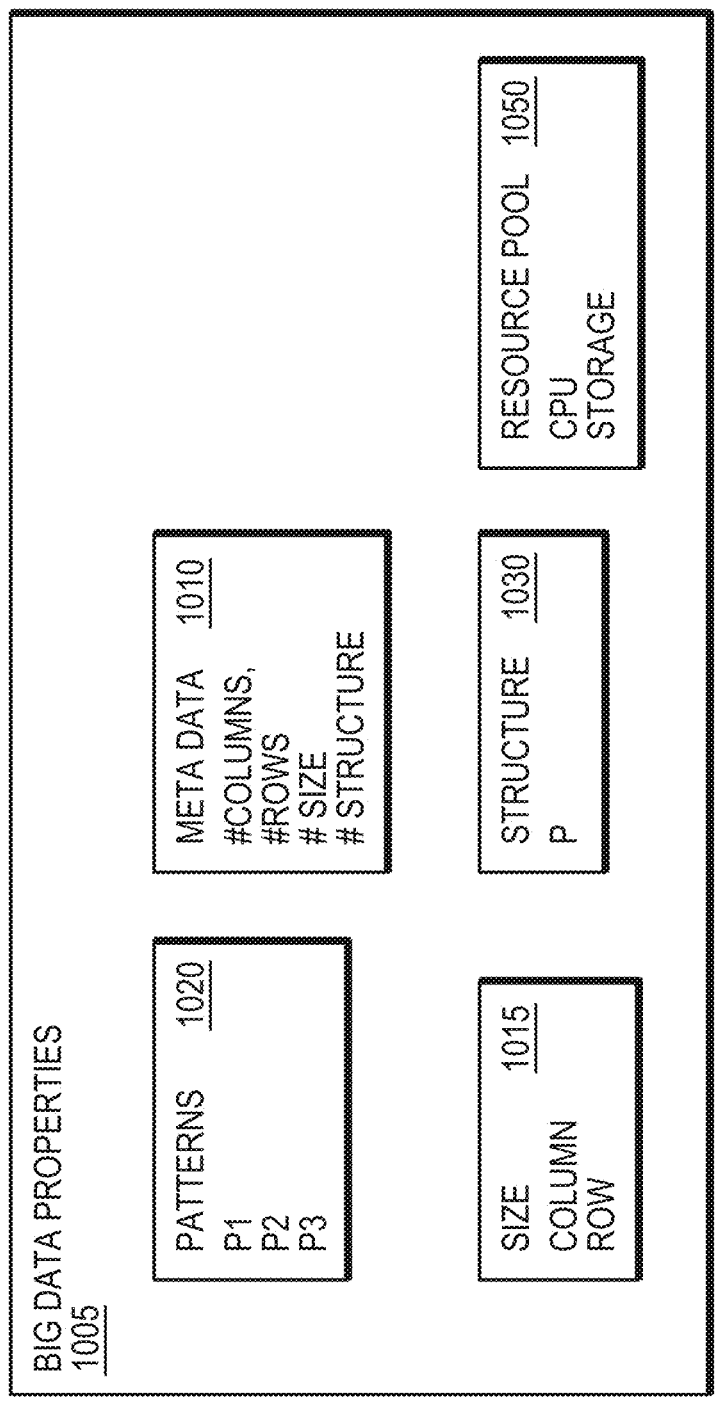
FIG. 10 is a simplified illustration of a model representation of a Big Data Properties, in accordance with an embodiment of the present disclosure.

Refer now to the example embodiment of FIG. 10. In the example embodiment of FIG. 10, the digital pathology example may be modeled according to the techniques of the current disclosures. In the embodiment of FIG. 10, each pathology image may be represented as big data class 1005, such as class 125 of FIG. 1. Each big data class, may have a metadata object, such as metadata 1010. Metadata 1010 describes the data in the image, such as the number of columns, the number of rows of the data, the size of the image and the structure of the image. In FIG. 10, there is also patterns class 1020, that describes the patterns of the digital pathology image. There is also structure class 1030 that describes the structure of the digital pathology image. There also is resource pool 1050, which describes the resources that relate to the image. In certain embodiments, the resource pool may describe the necessary resources to perform analysis of the big data. In other embodiments the resource pool may describe the resources used to store and compute the big data.

Refer now to the example embodiment of FIG. 11, which illustrate an example application of the digital pathology image with the big data classes outlined in FIG. 10 and FIGS. 1-5. The metainformation class has meta info for 100 GB images 1105. Attributes 1110 of this class are the sources, creation time, file format, blocks, object store, database type, linked metadata list, growth rate, last used, analysis type list, analysis policy list, and compute resource.

Figure 12:
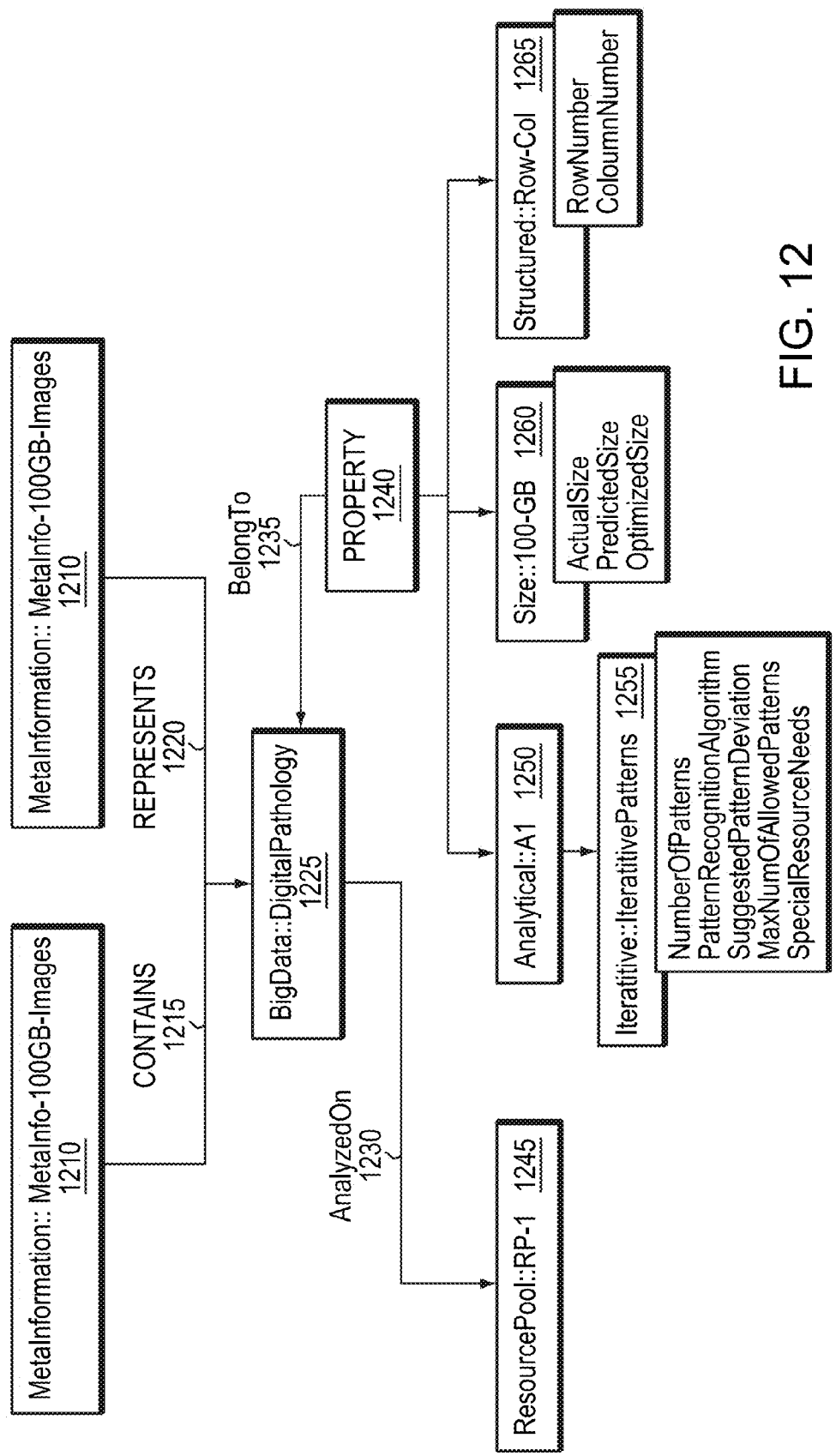
FIG. 12 is a simplified illustration of a model representation of Big Data for Pathology Slide Information, in accordance with an embodiment of the present disclosure.

Refer now to the example embodiment of FIG. 12, which illustrates an example of the big data model of FIG. 1 to digital pathology. Data Set class is 100 GB images 1205 contains 1215 Big Data Pathology 1225. Meta information 1210 is the meta information as described in FIG. 11 and Represents 1220 Big Data 1225. Properties 1240 are defined to be analytical properties 1250, size properties 1260, and structured 1265 and belong to Big Data 1225. Each of these classes is further populated with different attributes. Analytical 1250 also has Iterative Patterns 1255, which has attributes. Big Data 1225 is Analyzed on 1230 Resource Pool 1245.

In the embodiment of FIG. 12, the number of patterns could be populated with the number of patterns in the database. Similarly, the number of rows or columns may correspond to the number of rows or columns in a digital pathology sample. The algorithm used may be provided in that particular attribute—i.e. striping the data stored according to the metadata. How many rows and columns should be in the patterns and how many differ from those patterns may be stored as the suggested number of patterns. Information about the size such as the actual size predicted size and optimized size may be stored in the size.

Figure 13:
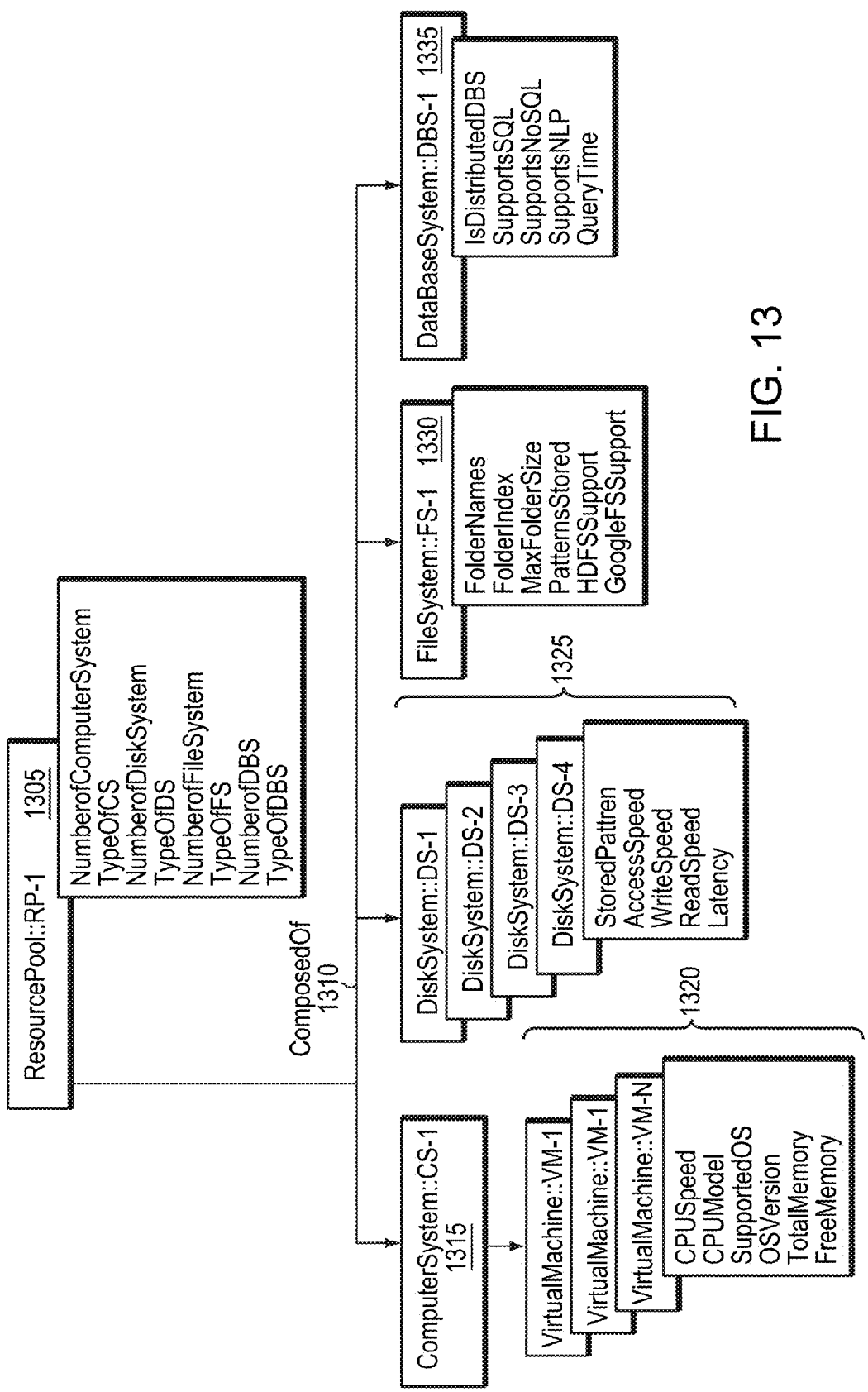
FIG. 13 is a simplified illustration of a model representation of Resources for a Big Data model, in accordance with an embodiment of the present disclosure.

Refer now to the example embodiment of FIG. 13. FIG. 13 shows an example embodiment of the resource class information. Resource pool 1305 has a number of attributes such as number of computer system and number of disks. Resource Pool 1305 is composed 1310 of disks systems 1325, file systems 1330, database systems 1335, and computer systems 1315. Each of these classes may be composed of other classes and may have different attributes. For example, computer system 1315 has a number of Virtual Machines 1320.

Figure 14:
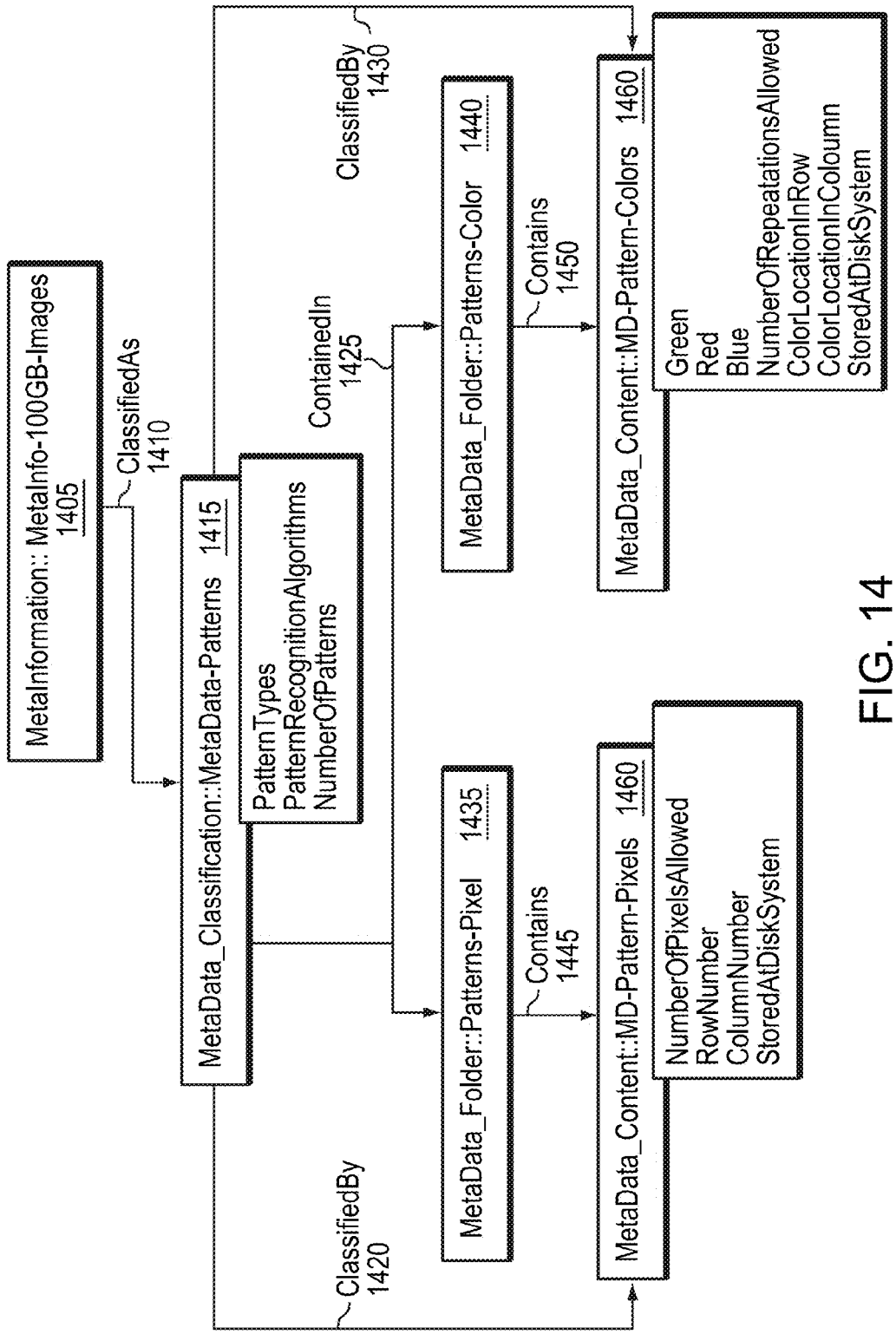
FIG. 14 is a simplified illustration of a model representation of MetaData information for a Big Data model of Digital pathology slide data, in accordance with an embodiment of the present disclosure.

In the embodiment of FIG. 14, the resource pool may be made up of the resources available to process the big data system. In FIG. 13, the available computer systems is a set of virtual machines, where each virtual machine has a cpu speed, model OS, memory total, and free memory. The resource pool may have other attributes and parameters, such as the disk or file systems.

Refer now to the Example embodiment of FIG. 14. FIG. 14 illustrates an example application of the metadata model of FIG. 2 to the digital pathology big data set. Metadata Information 1405 may be classified as 1410 meta data classification 1415. For example, the metadata classification 1415 may be made up of meta data patterns which have the attributes pattern types, pattern recognition algorithms, and number of patterns. Meta data classification 1415 may be classified by 1420 metadata content 1455. MetaData content 1455 may have a set of attributes such as column number and row number. Meta data classification 1415 may be classified by 1430 metadata content 1460, which has attributes such as color and disk location. Meta data classification 1415 may be contained in metadata folder 1435, which may contain 1445 metadata content 1455. Meta data classification 1415 may be contained in metadata folder 1440, which may contain 1450 metadata content 1460.

The example embodiment of FIG. 14 also may have different types of data populating the model. For the digital pathology data sample, the number of max pixels allowed, row numbers, column numbers may all be part of the metadata pixels. The types of colors may be stored Refer now to the example embodiment of FIG. 15, which represents an example implementation of creating big data model. The Big Data model (step 1505) may be extended to reflect the domain, and inherent domain classes may introduce additional attributes (step 1510). The model may be implemented using a modeling framework in a distributed architecture (step 1515). The model may be populated and data may be distributed based on the meta-data information (step 1520). Additional classes and attributes may be added based on the newly populated big data instance (step 1525). Consistency of the model may be checked (step 1530). If the model is consistent, the modeling may be finished, if the model is not consistent, the population may be performed again (step 1520)

Analysis

In certain embodiment, there may be different types of analysis performed on a big data set. In some embodiments, a type of analysis may be to analyze the data in the populated model to create more classes and further populate the model. In an example embodiment, this may include classifying the data into folders, such as is shown in FIG. 2. In other embodiments, a type of analysis may be an arithmetic analysis, such as the analysis outlined in FIG. 16. In further embodiments, another type of analysis may use the arithmetic analysis and the classifying analysis to provide further analysis of the Big Data Model data.

Figure 16:
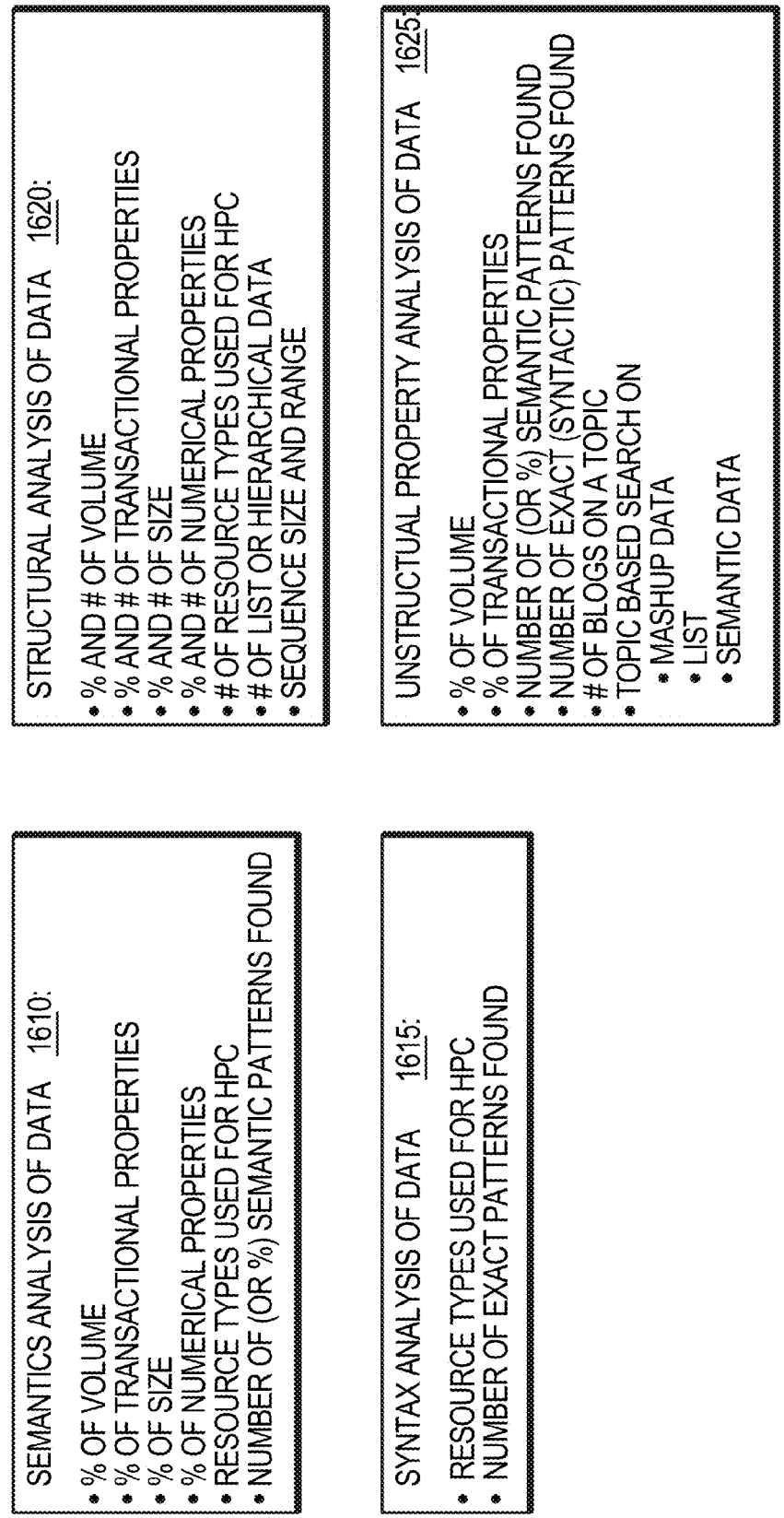
FIG. 16 is a simplified illustration of a model representation of Analytical properties for a Big Data model, in accordance with an embodiment of the present disclosure.

Refer now to the example embodiment of FIG. 16. In the example embodiment of FIG. 16, some preliminary analysis of the Big Data modeled may be performed. A semantic analysis of the data 1610 may be performed. The semantics analysis may be based on the metadata and may result in calculating the percentage of volume of the metadata, the percentage of transactions, the size, the percentage of numerical properties, the resource types for high performance computing (HPC) and the percentage of semantic properties found, where the percentage may be in comparison to another Big Data set.

In certain embodiments, a set of Big Data may be analyzed. In some embodiments, the properties and the meta-information associated with the Big Data may be analyzed. In at least some embodiments, the meta-information and the properties-information of the Big Data may be decoupled to enable this information be stored and analyzed. In certain embodiments, one of the properties associated with Big Data, the Key-Value pair may be used as indexes for the content associated with Big Data. In a particular embodiment of analysis may be finding all the Big data that has a certain key-value pair. In this embodiment, by having the Key-Value pair de-coupled or extracted from the content, analysis may be performed on the key-value pair without accessing/traversing the entire set.

A structural analysis of the data 1620 may be performed. The structural analysis may denote the percentage and amount of volume, the percentage and number of transactional properties, the number and percentage of size, the number and percentage of numerical properties. The number of resource types used for HPC, the number of list or hierarchical data, and the sequential size and range of the data.

A syntactical analysis of the data 1615 may also be performed to denote the resource types used for HPC and the number of patterns found in the data. As well, an unstructured property analysis of the data 1625 may be performed to indicate the percentage of volume that is unstructured, what percentage of the transactional properties are unstructured, what number or percentage of semantic patterns found, number of exact syntactical patters found, number of blogs on a topic, topic based searched on mash-up data, list, and semantic data. In some embodiments, the analysis performed at an aggregate level, such as in FIG. 16, may enable creation of a dashboard that represents high level summary information about the Big Data.

Figure 17:
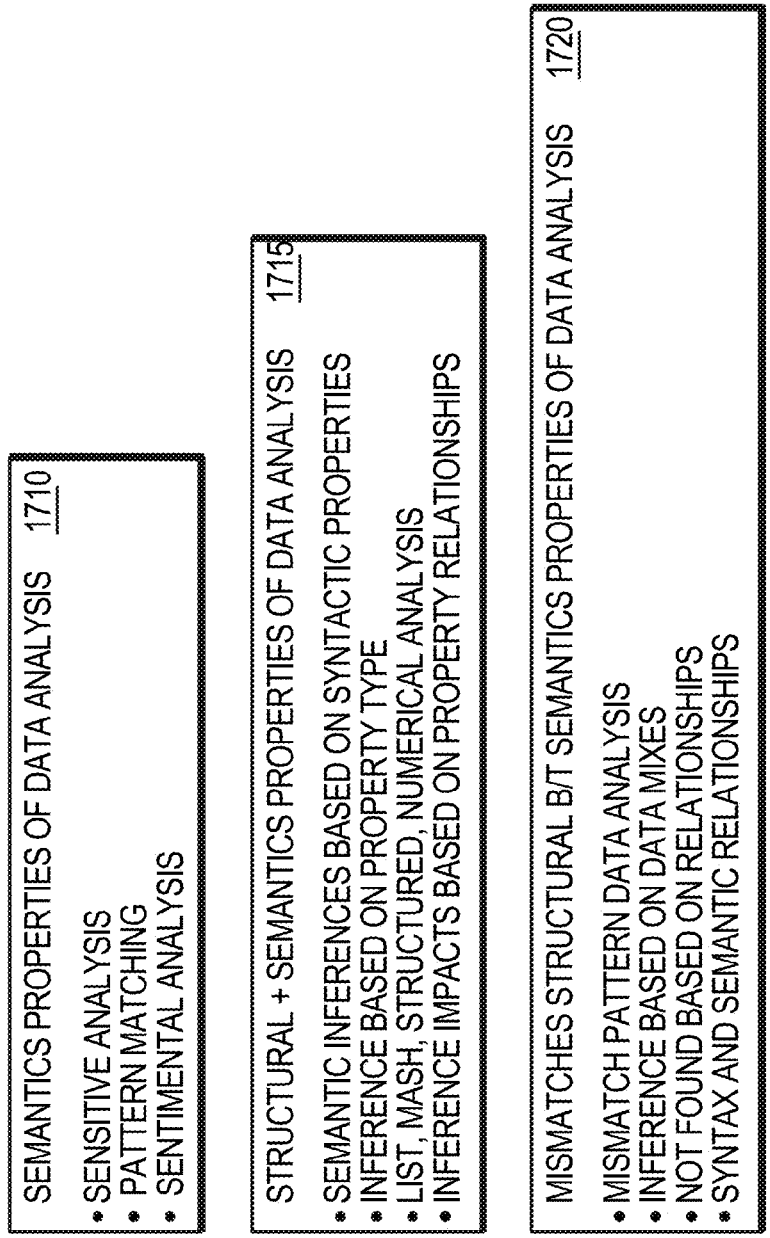
FIG. 17 is simplified illustration of further a model representation of Analytical properties for a Big Data model, in accordance with an embodiment of the present disclosure.

Refer now to the example embodiment of FIG. 17. In this example embodiment, the semantic properties of the data analysis 1710 may be performed to determine a sensitive analysis, pattern matching and sentimental analysis. As well, the structural and semantics properties of the data analysis 1715 may be performed. The structural and semantics properties may include semantic interferences based on syntactic properties, inference based on property type, list mash, structured numerical analysis, and inference impacts based on property relationships. As well, a mismatch structural analysis of the semantic properties of the data analysis 1720 may be performed to determine the mismatch pattern data analysis, inference based on data mixes, information not found based on relationships, and syntax and semantic relationships. Referring as well to FIG. 2, the semantic data may also be classified into folders and contents as exemplified in FIG. 2.

Figure 18:
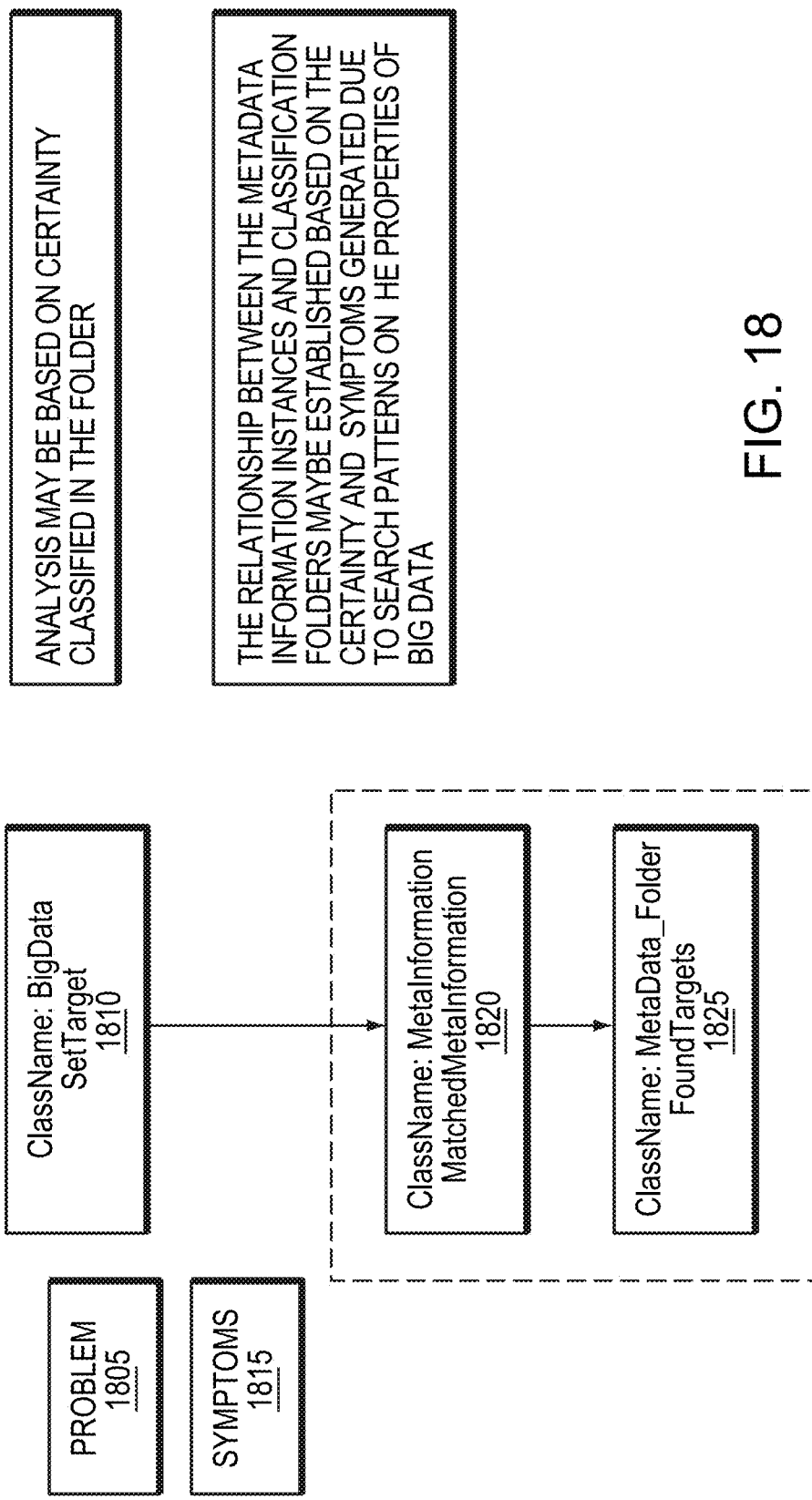
FIG. 18 is simplified illustration of a model representation of an analysis model for a Big Data model, in accordance with an embodiment of the present disclosure.

Refer now to the example embodiment of FIG. 18. A problem, such as problem 1805, may be mapped to the big data target set 1810. A correlation to symptoms 1815 may be created by matching the meta information 1820 by creating found targets 1825.

In certain embodiments, the analysis of problems to symptoms may include a temporal or transactional analysis with other events or times. In a particular embodiment, a set of Google transactions, such as people who bought a particular item, may be correlated with a time in a month or a particular month. In further embodiments, the Google transactions may be correlated with other extraneous events, such as weather or political phenomenon. In a particular embodiment, transactions related to buying of financial instruments, such as stocks or bonds or switching to buying stocks and bonds, could be correlated to political speeches motioning certain topics. Generally, such correlations were not previously possible as conventional techniques were not able to either model or correlate such large amounts of data.

In another embodiment, the number and type of twitter transactions may be correlated with outside events. In a particular embodiment, the number of twitter transactions may be correlated to a particular presidential speech. In another embodiment, the number of tweets may be correlated to a particular event, such as the capture of a particular criminal or fugitive. Another embodiment may correlate events usually not considered with financial transactions. In a certain embodiment, outside events such as political speeches and general market data may be correlated to the transactional data of a particular stock, such as an automobile stock, to note how the stock performs based on conditions that may not otherwise be considered.

In further embodiments, health symptoms may be correlated to specific events. In some embodiments, the outbreak of an infectious disease, such as identified through digital pathology samples, may be correlated to a different set of events. For example, a particular embodiment may link the outbreak of a certain disease to a particular weather condition in a particular location and climate or a disease outbreak may be linked to weather and time. In further embodiments, disease breakouts and rates, such as cancer, may be inferred to be linked to other environmental factors such as level of industrialization in a geographic location or even type of industrialization per area.

In a particular embodiment, cancer data across several geographic locations in the US in terms of patterns and type of cancer shown through digital pathology images, may be inferred to be linked across a particular type of industry in those geographic locations. In certain embodiments, an inference may be made based on a single big data set. In other embodiments, an inference may be made by correlating across two or more big data sets. In further embodiments, the big data may be used to create an impact analysis, such as determining what group of people or what geographic location may be next impacted by a weather condition or the spread of an infectious disease. In other embodiments, analysis of the Big Data model may include determining if there is a data mismatch of the data, such as digital pathology samples that do not conform to a disease or level of infection of that disease.

In certain embodiments, a digital pathology analysis may also include pattern matching to determine where the areas of interest are on a number of digital pathology slides. In further embodiments, a digital pathology analysis may automatically correlate digital pathology images into different stages of disease, such as the different types or progression of Alzheimer's disease. In some embodiments, a digital pathology sentimental analysis with may denote spots that are outside of the norm in the digital pathology sample that may require further analysis but does not match a particular pattern. In further embodiments, the analysis of an infectious disease may be a type of sensitivity analysis to determine what level denotes an outbreak of the disease.

Figure 19:
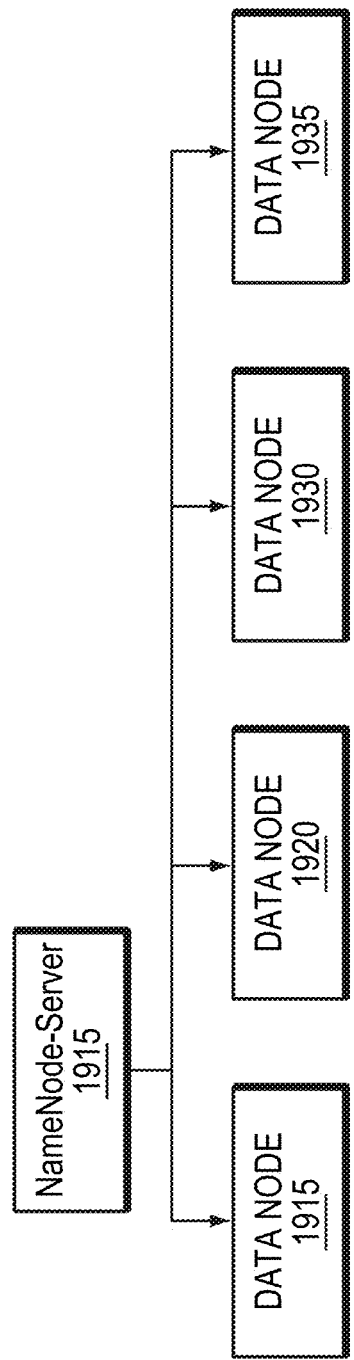
FIG. 19 is simplified illustration of nodes and a name node server for use in processing a Big Data Model, in accordance with an embodiment of the present disclosure.

Refer now to the example embodiment of FIG. 19. FIG. 19 outlines a sample architecture that may be used to perform analysis of Big Data. The architecture of FIG. 19 may be similar to that of the Hadoop architecture. FIG. 19 has Name Node server 1905 and several data nodes, 1915, 1920, 1930, and 1935. Name Node 1905 may be used to map and distribute the data of the Big Data to each of the data nodes, 1915, 1920, 1930, and 1935 (step 2005). In certain embodiments, Name Node 1905 may create hash values for each pierce of data in the data set and assign, based on the hash, each piece of data to a particular data node. Name Node 1905 may instruct each data node to perform some analysis (Step 2010). Name Node 1905 may receive the analysis from data nodes 1915, 1920, 1930, and 1935 (Step 2015). Name Node 1905 may summarize of perform post processing on the analyzed data (Step 2020).

In certain embodiments, analysis software may be pushed to the data nodes as well as the data. In different embodiments, the analysis performed by nodes may differ. In a particular embodiment, EMC SMARTS may be the analysis engine for the analysis. In other embodiments, EMC Greenplum may provide an analysis engine for the analysis. In further embodiments, different types of analysis may be used.

Figure 20:
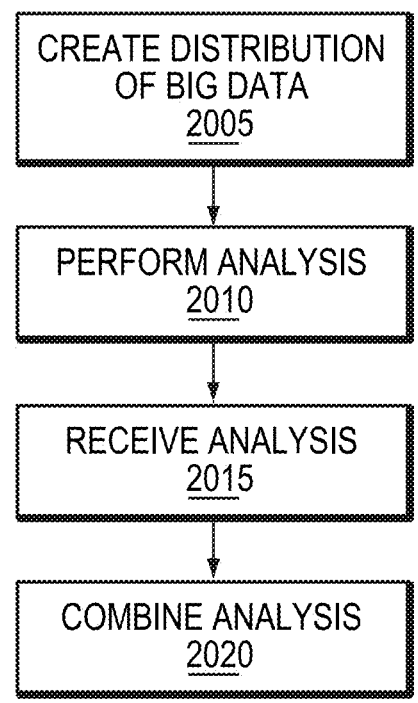
FIG. 20 is a simplified method for analysis of a Big Data model, in accordance with an embodiment of the present disclosure.
Figure 21:
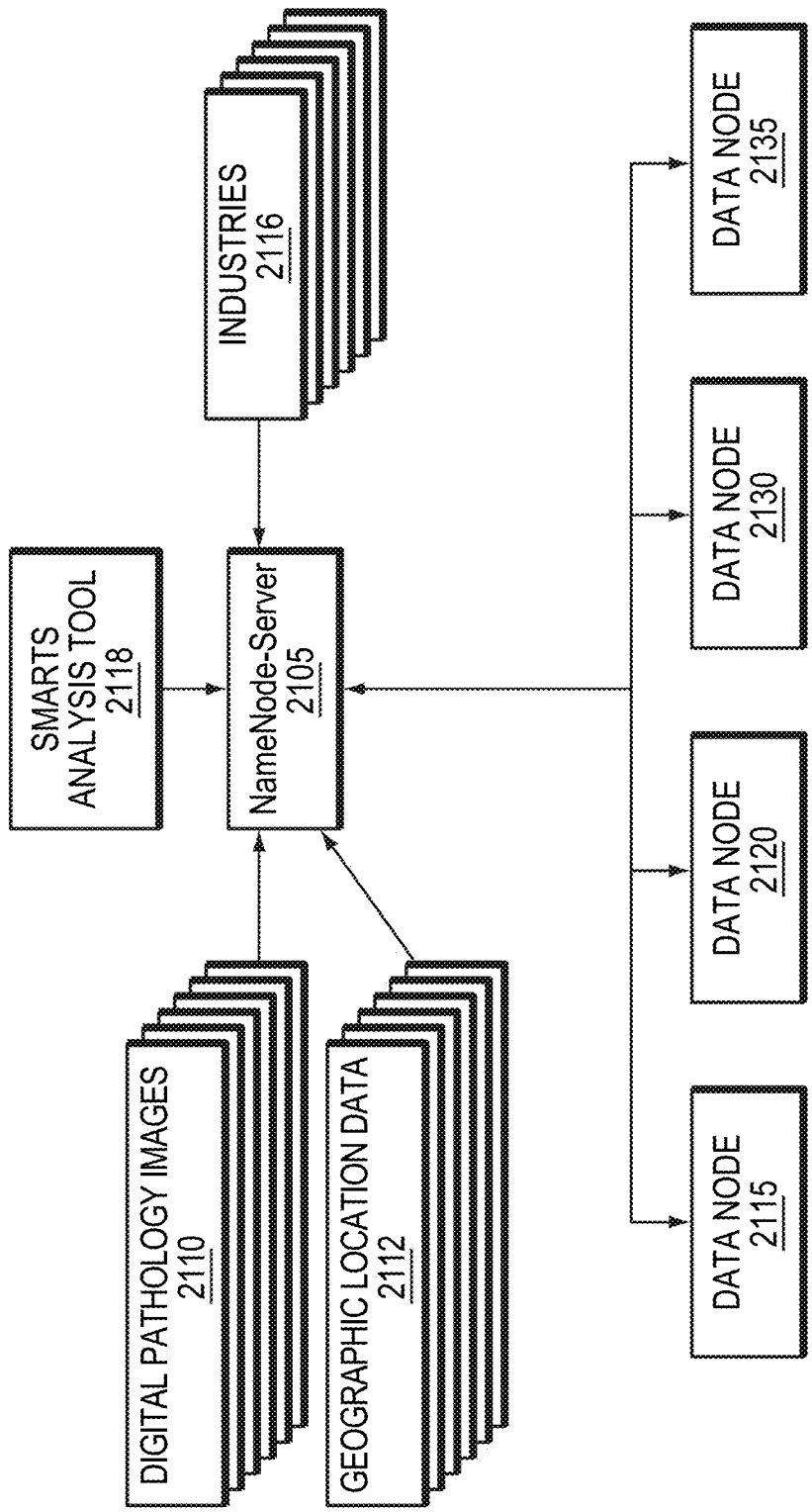
FIG. 21 is simplified illustration of nodes and a name node server for use in processing a Big Data Model of Digital Pathology images, in accordance with an embodiment of the present disclosure.

Refer now to the example embodiments of FIGS. 20 and 21. In the example embodiment of FIG. 21, there are three Big Data Sets, Digital pathology images 2110, Geographical location data 2112, and a set of industries 2116 and information about these industries. As well there is a SMARTS Analysis Tool 2118. Name Node Server 2105 determines how to divide and distribute the data for analysis on data nodes 2115, 2120, 2130, and 2135. NameNode Server creates a distribution of the SMARTS Analysis tool 2118 to each of the Data Nodes along with the Digital Pathology Images 2110, Geographic Location Data 2112, and Industries 2116 (step 2005) and each data node gets the information and analysis tool associated with its distribution. Data nodes 2115, 2120, 2130, and 2135 perform analysis using SMARTS Analysis Tool on the provided data (step 2110). The analysis provided may be to perform pattern matching on the digital pathology images to determine what type of disease may be present in the image. The analysis may further correlate the disease with the geographic location data to determine where certain diseases exist. Sensitivity analysis may be performed to see if there are any outliers or anomalies in the digital pathology data that would need to be further analyzed. The analysis may further correlate the digital pathology data with industries in those areas to determine if there are higher types of disease for certain types of industries in certain locations. Name Node 2105 receives the analysis from the Data Nodes 2115, 2120, 2130, and 2135 (step 2105). Name Node 2105 combines the analysis from the data nodes. Name Node 2105 may provide further analysis on the analysis of the data nodes.

Figure 22:
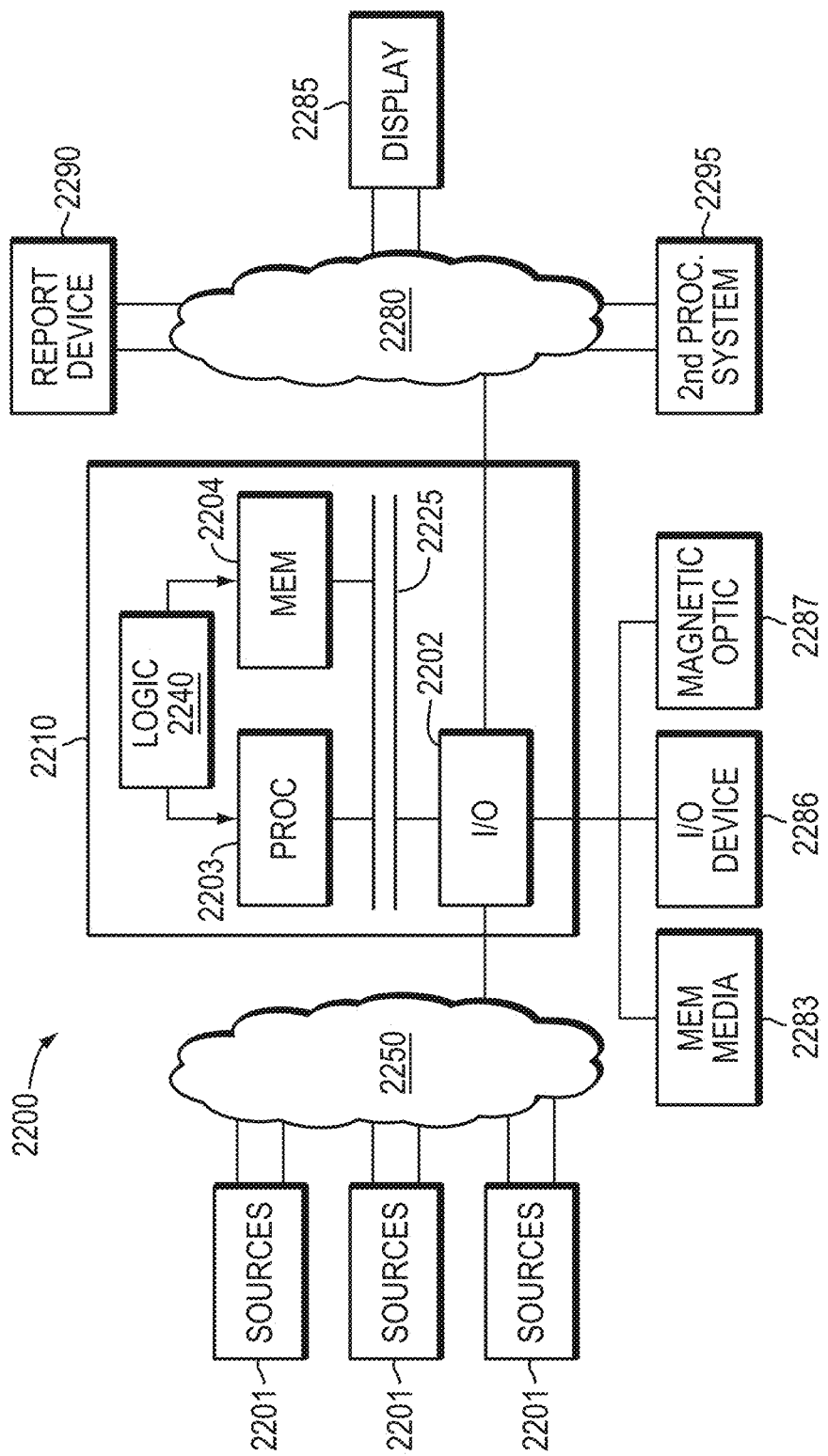
FIG. 22 is an example of an embodiment of an apparatus that may utilize the techniques described herein, in accordance with an embodiment of the present disclosure.
Figure 23:
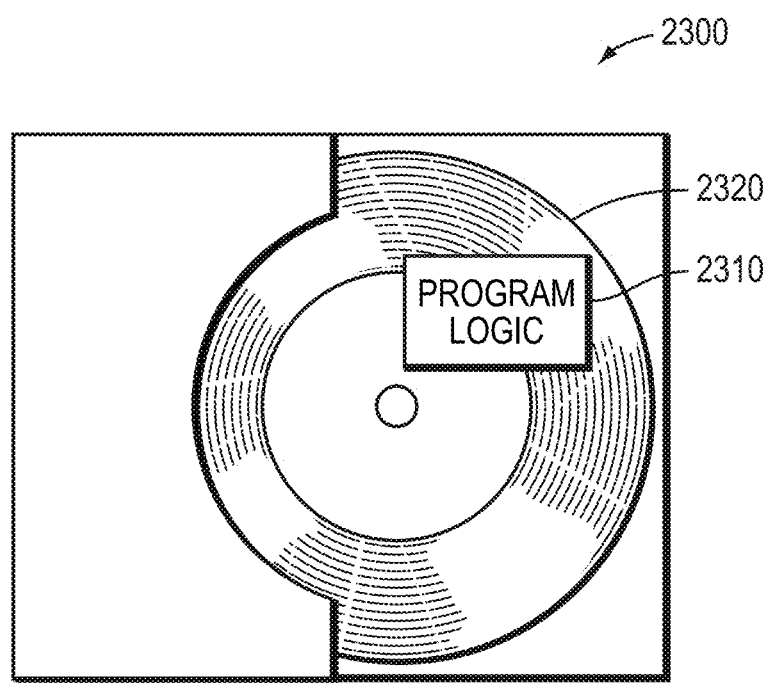
FIG. 23 is an example of an embodiment of a method embodied on a computer readable storage medium that may utilize the techniques described herein, in accordance with an embodiment of the present invention.

The methods and apparatus of this invention may take the form, at least partially, of program code (i.e., instructions) embodied in tangible media, such as floppy diskettes, CD-ROMs, hard drives, random access or read only-memory, or any other machine-readable storage medium. When the program code is loaded into and executed by a machine, such as the computer of FIG. 22, the machine becomes an apparatus for practicing the invention. When implemented on one or more general-purpose processors, the program code combines with such a processor 2203 to provide a unique apparatus that operates analogously to specific logic circuits. As such a general purpose digital machine can be transformed into a special purpose digital machine. FIG. 23 shows Program Logic 2334 embodied on a computer-readable medium 2330 as shown, and wherein the Logic is encoded in computer-executable code configured for carrying out the reservation service process of this invention and thereby forming a Computer Program Product 2300. The logic 2334 may be the same logic 2240 on memory 2204 loaded on processor 2203. The program logic may also be embodied in software modules, as modules, or as hardware modules.

Figure 15:
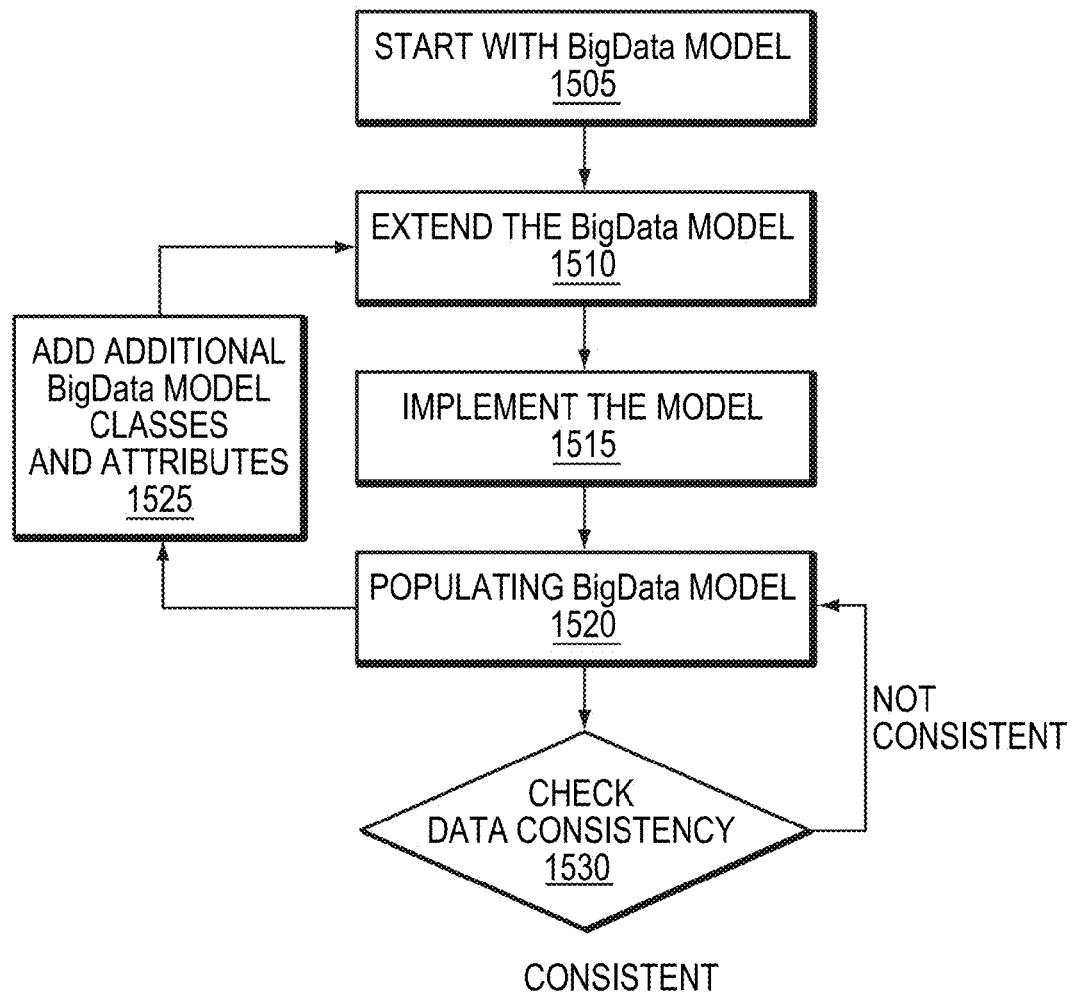
FIG. 15 is a simplified method for use in modeling Big Data, in accordance with an embodiment of the present disclosure.

The logic for carrying out the method may be embodied as part of the system described below, which is useful for carrying out a method described with reference to embodiments shown in, for example, FIG. 12 and FIG. 15. For purposes of illustrating the present invention, the invention is described as embodied in a specific configuration and using special logical arrangements, but one skilled in the art will appreciate that the device is not limited to the specific configuration but rather only by the claims included with this specification.

Although the foregoing invention has been described in some detail for purposes of clarity of understanding, it will be apparent that certain changes and modifications may be practiced within the scope of the appended claims. Accordingly, the present implementations are to be considered as illustrative and not restrictive, and the invention is not to be limited to the details given herein, but may be modified within the scope and equivalents of the appended claims.

What is claimed is:

1. A computer implemented method for analyzing a Big Data dataset, the method comprising:
    extending a big data model to create representations for the Big Data dataset; wherein the Big Data Model enables analysis of the data in the Big Data dataset; wherein the Big Data Model including a plurality of representations;
    using the Big Data model to decouple properties and metadata from the Big Data dataset; wherein each of the properties represent part of the Big Data dataset to enable processing and analysis; wherein the metadata enables calculation of summary information for the Big Data dataset; wherein the representations include meta Information, metadata classification, and metadata content; wherein one or more of the representations of the Big Data Model represents the hierarchy of the data Big Data Dataset; wherein one or more of the representations of the Big Data Model represents the classification of the of the data Big Data Dataset;
    performing analysis on the big data dataset by applying a set of analytical tools to the Big Data Model; wherein the analysis further includes pre-analyzing the Big Data Dataset to create further representations and populating the further representations in the Big Data Model based on the pre-analyzing.

2. The method of claim 1 wherein the selected at least one analysis performed is a semantics analysis of the data of the Bid Data dataset and where at least one semantics analysis is selected from the group consisting of percentage of volume, percentage of transactional properties, percentage of size, percentage of numerical properties, resource types used for high power computing, number or percentage of semantic patterns found.

3. The method of claim 1 wherein the selected at least one analysis performed is a semantics analysis of the data of the Bid Data dataset and where at least one semantics analysis is selected from the group sensitive analysis, pattern matching, and sentimental analysis.

4. The method of claim 1 further comprising:
    providing a mapping between problems of the Big Data dataset and a symptoms of the Big Data dataset;
    determining at least one problem based on at least one symptom by determining, in an automated manner, a measure between each of a plurality of relationship values associated with problems and the symptoms.

5. The method of claim 1 further comprising:
    splitting, based on the Big Data model, the Big Data dataset into a number of groups at a summing node; wherein each group of the groups represents a portion of the Big Data dataset;
    distributing, based on the Big Data model, the groups representing the Big Data dataset to nodes based on the splitting;
    performing analysis, at each respective node of the nodes of the respective group of the groups for the respective node;
    receiving the analysis of the groups by the nodes at the summing node;
    combining, at the summing node, the analysis of each of the groups at the node.

6. The method of claim 1 wherein the non-specific representations further include Property type, analytical, volume, and structure.

7. The method of claim 6 wherein the Big Data Model is enabled to represent both structured and unstructured data without converting the unstructured data into structured data; wherein structured data is able to be stored in a database field and wherein unstructured data is not able to stored in a database field.

8. A computer program product for use in replication comprising:
    a non-transitory computer readable medium encoded with computer executable program code for migration of data, the code configured to enable the execution of:
    extending a big data model to create representations for the Big Data dataset; wherein the Big Data Model enables analysis of the data in the Big Data dataset; wherein the Big Data Model including a plurality of representations;
    using the Big Data model to decouple properties and metadata from the Big Data dataset; wherein each of the properties represent part of the Big Data dataset to enable processing and analysis; wherein the metadata enables calculation of summary information for the Big Data dataset; wherein the representations include meta Information, metadata classification, and metadata content; wherein one or more of the representations of the Big Data Model represents the hierarchy of the data Big Data Dataset; wherein one or more of the representations of the Big Data Model represents the classification of the of the data Big Data Dataset;
    performing analysis on the big data dataset by applying a set of analytical tools to the Big Data Model; wherein the analysis further includes pre-analyzing the Big Data Dataset to create further representations and populating the further representations in the Big Data Model based on the pre-analyzing.

9. The program product of claim 8 wherein the selected at least one analysis performed is a semantics analysis of the data of the Bid Data dataset and where at least one semantics analysis is selected from the group consisting of percentage of volume, percentage of transactional properties, percentage of size, percentage of numerical properties, resource types used for high power computing, number or percentage of semantic patterns found.

10. The program product of claim 8 wherein the selected at least one analysis performed is a semantics analysis of the data of the Bid Data dataset and where at least one semantics analysis is selected from the group sensitive analysis, pattern matching, and sentimental analysis.

11. The program product of claim 8 wherein the executable program code is further configured for execution of:
    providing a mapping between problems of the Big Data dataset and a symptoms of the Big Data dataset;
    determining at least one problem based on at least one symptom by determining, in an automated manner, a measure between each of a plurality of relationship values associated with problems and the symptoms.

12. The program product of claim 8 wherein the executable program code is further configured for execution of splitting, based on the Big Data model, the Big Data dataset into a number of groups at a summing node; wherein each group of the groups represents a portion of the Big Data dataset distributing, based on the Big Data model, the groups representing the Big Data dataset to nodes based on the splitting;

performing analysis, at each respective node of the nodes of the respective group for the respective node;

receiving the analysis of the groups by the nodes at the summing node;

combining, at the summing node, the analysis of each of the groups at the node.

13. The computer program product of 8 wherein the non-specific representations further include Property type, analytical, volume, and structure.

14. The computer program product of claim 13 wherein the Big Data Model is enabled to represent both structured and unstructured data without converting the unstructured data into structured data; wherein structured data is able to be stored in a database field and wherein unstructured data is not able to stored in a database field.

15. An apparatus comprising:
one or more processors;
logic, stored on a non-transitory medium, configured when loaded across the one or more processors to enable the execution of:
extending a big data model to create representations for the Big Data dataset; wherein the Big Data Model enables analysis of the data in the Big Data dataset; wherein the Big Data Model including a plurality of representations;
using the Big Data model to decouple properties and metadata from the Big Data dataset; wherein each of the properties represent part of the Big Data dataset to enable processing and analysis; wherein the metadata enables calculation of summary information for the Big Data dataset; wherein the representations include meta Information, metadata classification, and metadata content; wherein one or more of the representations of the Big Data Model represents the hierarchy of the data Big Data Dataset; wherein one or more of the representations of the Big Data Model represents the classification of the of the data Big Data Dataset;
performing analysis on the big data dataset by applying a set of analytical tools to the Big Data Model; wherein the analysis further includes pre-analyzing the Big Data Dataset to create further representations and populating the further representations in the Big Data Model based on the pre-analyzing.

16. The apparatus of claim 15 wherein the selected at least one analysis performed is a semantics analysis of the data of the Bid Data dataset and where at least one semantics analysis is selected from the group consisting of percentage of volume, percentage of transactional properties, percentage of size, percentage of numerical properties, resource types used for high power computing, number or percentage of semantic patterns found.

17. The apparatus of claim 15 wherein the selected at least one analysis performed is a semantics analysis of the data of the Bid Data dataset and where at least one semantics analysis is selected from the group sensitive analysis, pattern matching, and sentimental analysis.

18. The apparatus of claim 15 the logic further comprising:
a module enabling a mapping to be performed between problems of the Big Data dataset and a symptoms of the Big Data dataset;
a module enabling automatic determination of at least one problem based on at least one symptom by automatically determining a measure between each of a plurality of relationship values associated with problems and the symptoms.

19. The apparatus of claim 15 the logic further comprising:
a module enabling the Big Data dataset to be split, based on the Big Data model, into a number of groups at a summing node; wherein each group of the groups represents a portion of the Big Data dataset;
a module enabling the groups representing the Big Data dataset to be distributed, based on the Big Data model, to nodes based on the splitting;
one or more modules enabling analysis of the respective group for the respective node to be performed at each respective node of the nodes;
a module enabling the summing node to receive the analysis of the groups from each node of the nodes;
a module enabling the analysis to be combined at the summing node.

20. The apparatus of 15 wherein the non-specific representations further include Property type, analytical, volume, and structure.

* * * * *